USOO5766481A

United States Patent [19]
Zambias et al.

[11] Patent Number: 5,766,481
[45] Date of Patent: Jun. 16, 1998

[54] METHOD FOR RAPID PURIFICATION, ANALYSIS AND CHARACTERIZATIONS OF COLLECTIONS OF CHEMICAL COMPOUNDS

[75] Inventors: Robert Anthony Zambias, Lexington, Mass.; David Arthur Boulton, Tinton Falls, N.J.; Jay Ping Chiang, Boston, Mass.

[73] Assignee: Arqule, Inc., Medford, Mass.

[21] Appl. No.: 801,664

[22] Filed: Feb. 18, 1997

Related U.S. Application Data

[63] Continuation of Ser. No. 418,233, Apr. 6, 1995, abandoned.

[51] Int. Cl.[6] ................................................... B01D 15/08
[52] U.S. Cl. ........................... 210/656; 210/659; 436/161
[58] Field of Search ........................... 210/635, 656, 210/659, 198.2; 436/161; 530/413, 417

[56] References Cited

U.S. PATENT DOCUMENTS

| | | | |
|---|---|---|---|
| 3,410,880 | 11/1968 | Brockenhurst | 360/404.9 |
| 3,450,673 | 6/1969 | McKillip | 260/75 |
| 3,485,806 | 12/1969 | Bloomquist et al. | 260/80.3 |
| 3,488,327 | 1/1970 | Kollinsky et al. | 260/78.3 |
| 3,488,389 | 1/1970 | McKillip | 260/561 |

(List continued on next page.)

FOREIGN PATENT DOCUMENTS

| | | | |
|---|---|---|---|
| 0 185 493 | 6/1986 | European Pat. Off. | 210/198.2 |
| 0 212 617 | 4/1987 | European Pat. Off. | 210/198.2 |
| 63-17933 | 4/1988 | Japan | 210/198.2 |
| 1 181 218 | 2/1970 | United Kingdom | 210/198.2 |
| 1 265 163 | 3/1972 | United Kingdom | 210/198.2 |
| 93/20935 | 10/1993 | WIPO | 210/198.2 |

OTHER PUBLICATIONS

Tetrahedron Letters, 27, 6319 (1986).
Kardiologisisa, "Bioelectrical Mechanism", vol. 31, No. 7, 1991, pp. 52–55.
Kardiologisisa, vol. 30, No. 8, 1990, pp. 69–72.
J. Hetegel Chem., 1972, 9, 687–690, "Aminimides IX(1). A general Synthesis of 1–Substituted–2–imidazolidinones(2)", by David Aelony et al.
J. Org. Chem., vol. 41, No. 4, 1976, 715–716, "Acyl Migration in 2–Hydroxylalkyl Aminimides", by Meir Asscher.

(List continued on next page.)

*Primary Examiner*—Ernest G. Therkorn
*Attorney, Agent, or Firm*—Pennie & Edmonds LLP

[57] ABSTRACT

The present invention relates to a method for the processing of molecules by determining one or more selection parameters for a plurality of molecules; selecting a compatible grouping of molecules based on the selection parameters to form a set; forming a mixture of molecules of interest from the set; and resolving the mixture to fractionate the molecules of interest. The preferred method utilizes HPLC chromatography column to resolve and purify molecules which have different retention times.

19 Claims, 6 Drawing Sheets

U.S. PATENT DOCUMENTS

| | | | |
|---|---|---|---|
| 3,499,032 | 3/1970 | Clemens et al. | 260/561 |
| 3,511,894 | 5/1970 | Markert | 260/875 |
| 3,527,802 | 9/1970 | Slagel | 260/561 |
| 3,555,095 | 1/1971 | Slagel | 260/584 |
| 3,565,868 | 2/1971 | Sedor et al. | 260/78.3 |
| 3,567,725 | 3/1971 | Grabowski et al. | 260/250 |
| 3,583,950 | 6/1971 | Kollinsky et al. | 260/78 |
| 3,598,790 | 8/1971 | Kollinsky et al. | 260/78.3 |
| 3,641,145 | 2/1972 | Culbertson | 260/558 |
| 3,664,990 | 5/1972 | Slagel | 260/85.5 |
| 3,671,473 | 6/1972 | Sedor et al. | 260/18 |
| 3,676,453 | 7/1972 | Pines et al. | 260/307 |
| 3,704,128 | 11/1972 | Koda et al. | 96/50 |
| 3,706,797 | 12/1972 | McKillip et al. | 260/558 |
| 3,706,800 | 12/1972 | Hartlage et al. | 260/561 |
| 3,715,343 | 2/1973 | Slagel et al. | 260/88.1 |
| 3,728,387 | 4/1973 | Freis et al. | 260/561 |
| 3,756,994 | 9/1973 | Culbertson | 260/82.1 |
| 3,781,319 | 12/1973 | Wawzonek et al. | 260/453 |
| 3,794,495 | 2/1974 | Ishihara et al. | 96/87 |
| 3,803,220 | 4/1974 | Gasman | 260/518 |
| 3,811,887 | 5/1974 | Ishihara et al. | 96/50 |
| 3,818,065 | 6/1974 | Schoellkopf et al. | 260/464 |
| 3,828,007 | 8/1974 | Throckmorton | 260/75 |
| 3,850,969 | 11/1974 | Grimm et al. | 260/404.5 |
| 3,893,974 | 7/1975 | Niino et al. | 260/47 |
| 3,898,087 | 8/1975 | Brutchen et al. | 96/33 |
| 3,904,749 | 9/1975 | McKillip | 424/71 |
| 3,925,284 | 12/1975 | Carleton et al. | 260/2.5 |
| 3,934,029 | 1/1976 | Kabara | 424/320 |
| 3,934,031 | 1/1976 | Kabara | 424/320 |
| 3,934,035 | 1/1976 | Kabara | 424/320 |
| 3,946,131 | 3/1976 | Biefeld et al. | 428/378 |
| 3,948,866 | 4/1976 | Pennewiss et al. | 260/79.3 |
| 3,963,703 | 6/1976 | Culbertson | 260/239 |
| 3,963,776 | 6/1976 | Middleton | 260/561 |
| 3,968,065 | 7/1976 | Morris et al. | 260/23.5 |
| 3,969,298 | 7/1976 | Gasman | 260/29.6 |
| 3,983,166 | 9/1976 | Samour | 260/481 R |
| 3,985,807 | 10/1976 | Grimm et al. | 260/561 |
| 4,005,055 | 1/1977 | Miron et al. | 260/47 |
| 4,016,340 | 4/1977 | Kolesinski et al. | 526/7 |
| 4,022,623 | 5/1977 | Fitzgerald et al. | 96/114 |
| 4,046,658 | 9/1977 | Brown | 204/181 |
| 4,067,830 | 1/1978 | Kresta | 260/2.5 |
| 4,070,348 | 1/1978 | Kriemer et al. | 260/79.3 |
| 4,073,725 | 2/1978 | Takeuchi | 210/659 |
| 4,078,901 | 3/1978 | Sung et al. | 44/64 |
| 4,080,206 | 3/1978 | Kolesinski et al. | 96/29 |
| 4,097,444 | 6/1978 | Teige et al. | 260/44 |
| 4,102,916 | 7/1978 | Falk | 260/501.12 |
| 4,122,159 | 10/1978 | Madrange et al. | 424/45 |
| 4,140,680 | 2/1979 | Sullivan | 526/287 |
| 4,162,355 | 7/1979 | Tsibris | 526/293 |
| 4,189,481 | 2/1980 | Kabara | 424/248.54 |
| 4,212,905 | 7/1980 | Talbris | 427/221 |
| 4,213,860 | 7/1980 | Tsibris | 210/31 |
| 4,217,364 | 8/1980 | Kabara | 424/320 |
| 4,260,705 | 4/1981 | Tsibris | 525/330 |
| 4,280,008 | 7/1981 | Schoellkopf et al. | 548/301 |
| 4,304,705 | 12/1981 | Heilmann et al. | 260/30.4 |
| 4,378,411 | 3/1983 | Heilmann et al. | 428/500 |
| 4,424,272 | 1/1984 | Taylor | 430/507 |
| 4,451,619 | 5/1984 | Heilmann et al. | 525/379 |
| 4,454,043 | 6/1984 | Ting | 210/659 |
| 4,485,236 | 11/1984 | Rasmussen et al. | 544/69 |
| 4,548,981 | 10/1985 | Kolesinski et al. | 524/555 |
| 4,563,467 | 1/1986 | Soler | 514/336 |
| 4,617,253 | 10/1986 | Taylor et al. | 430/323 |
| 4,624,995 | 11/1986 | Katritzky et al. | 525/452 |
| 4,645,711 | 2/1987 | Winslow | 428/355 |
| 4,667,012 | 5/1987 | Rasmussen et al. | 528/332 |
| 4,670,528 | 6/1987 | Taylor et al. | 526/263 |
| 4,695,608 | 9/1987 | Engler et al. | 525/308 |
| 4,705,824 | 11/1987 | Lin | 524/612 |
| 4,724,081 | 2/1988 | Kawahara et al. | 210/659 |
| 4,737,560 | 4/1988 | Heilmann et al. | 526/304 |
| 4,740,568 | 4/1988 | Katritzky et al. | 525/452 |
| 4,777,217 | 10/1988 | Rasmussen et al. | 525/279 |
| 4,777,276 | 10/1988 | Rasmussen et al. | 556/419 |
| 4,785,070 | 11/1988 | Rasmussen et al. | 528/73 |
| 4,806,250 | 2/1989 | Takata | 210/659 |
| 4,816,554 | 3/1989 | Katritzksy et al. | 528/210 |
| 4,837,157 | 6/1989 | Turnell | 210/659 |
| 4,841,021 | 6/1989 | Katritzky et al. | 528/407 |
| 4,852,969 | 8/1989 | Babirad et al. | 350/96.34 |
| 4,859,342 | 8/1989 | Shirasawa | 210/659 |
| 4,871,824 | 10/1989 | Heilmann et al. | 526/304 |
| 4,874,822 | 10/1989 | Rasmussen et al. | 525/279 |
| 4,898,923 | 2/1990 | Katritzky et al. | 528/73 |
| 4,948,715 | 8/1990 | Hulme-Lowe et al. | 430/495 |
| 4,950,397 | 8/1990 | Oquendo | 210/659 |
| 4,981,933 | 1/1991 | Fazio et al. | 526/260 |
| 5,013,795 | 5/1991 | Coleman et al. | 525/279 |
| 5,039,813 | 8/1991 | Fazio et al. | 548/228 |
| 5,066,559 | 11/1991 | Elmasry et al. | 430/111 |
| 5,075,352 | 12/1991 | Elmasry | 523/201 |
| 5,081,197 | 1/1992 | Heilmann et al. | 526/260 |
| 5,091,489 | 2/1992 | Heilmann et al. | 526/90 |
| 5,094,766 | 3/1992 | Kepuscinski et al. | 252/51.5 |
| 5,135,718 | 8/1992 | Kawaguchi | 210/659 |
| 5,138,071 | 8/1992 | Schoellkopf et al. | 548/537 |
| 5,147,957 | 9/1992 | Kumar | 528/15 |
| 5,149,806 | 9/1992 | Moren et al. | 544/72 |
| 5,157,108 | 10/1992 | Krepski et al. | 528/503 |
| 5,157,145 | 10/1992 | Schoellkopf et al. | 560/41 |
| 5,175,081 | 12/1992 | Krepski et al. | 430/617 |
| 5,185,102 | 2/1993 | Harelstad et al. | 252/582 |
| 5,194,623 | 3/1993 | Krepski et al. | 548/261 |
| 5,200,471 | 4/1993 | Coleman et al. | 525/326.9 |
| 5,223,435 | 6/1993 | Kohr | 210/659 |
| 5,277,871 | 1/1994 | Fujii | 210/656 |
| 5,306,426 | 4/1994 | Afeyan | 210/656 |
| 5,350,520 | 9/1994 | Kikumoto | 210/656 |
| 5,409,611 | 4/1995 | Kauver | 210/656 |
| 5,413,762 | 5/1995 | Hirano | 210/656 |
| 5,431,822 | 7/1995 | Temeuil | 210/659 |
| 5,443,734 | 8/1995 | Fetner | 210/656 |
| 5,508,204 | 4/1996 | Norman | 210/656 |

OTHER PUBLICATIONS

Biopolymers, vol. 17, 1693–1711 (1978), "Experimental Conformational Study of Two Peptides Containing a–Aminoisobutyric Acid. Crystal Structure of N–Acetyl–a–Aminoisobutyric Acid Methylamide" by A. Aubry et al.

Tetrahedron Letters No. 31, pp. 2691–2694, 1976, "Pyridines as Leaving Groups in Synthetic Transformations: Nucleophilic Displacements of Amino Groups, and Novel Preparations of Nitriles and Isocyanates", by J.B. Bapat et al.

University College, Hull, Sep. 27, 1952, pp. 453–456, "The Dehydration and Racemisation of N–Acyl–L –aspartic Acids by Acetic Anhydride", by C.C. Barker.

Acta Chem. Scand. B 33 (1979) No. 2, "Electron Deficient Heteroaromatic Ammonioamidates. XVII. N–(3–Quinazolinio)amindates. VI. The Photochemistry of N–(3OQuinazolinio)amidates in the Presence of α–Toluenethiol", by G. Barta–Szalai et al.

J. Chem. Socl. Perkin Trans. I 1983, "Electron Deficient Heteroaromatic Ammonioamides. Part 24.[1]. N–(Quinazolin–3–io)amindates. Part 11.[2] The Photochemistry of N–(6,7–Methylenedioxyquinazolin–3–io)amidates in Acetone", by Gizella Barta–Szalai et al.

J. Heterocyclic Chem., 23, 375, 1986, "Novel Synthesis of Pyrido[2,1-fl]–as–Triazinium System and its Zwitterionic Derivatives . . . ", by S. Batori.

J. Heterocyclic Chem., 25, 437 (1988), "Regioselectivity in Methylation and Phenylation of the Zwitterionic Pyrido[2, 1–f]–as–triazinium–1–and 3–olates and thiolates[1]", by Sandor Batori et al.

J. Heterocyclic Chem., 27, 1673 (1990), "Synthesis and Regiospecificity in Methylation of Pyrido[1,2–a] pyrazinium–1–and 3–olates and Pyrido[1,2–b] pyridazinium–2–and 4–olates [1]", by S. Batori et al.

J.C.S. Perkin II, 1978, 1173, "The Basicities of Substituted N–Trimethylammoniophenylacetamidates and N–Trimethylammoniocinnamamidates. The Hammett Correlations and the Thermodynamics of Protonation", by William H. Beck.

J.C.S. Perkin II, 1976, "The Basicities of N–Trimethylammonioacetamidate and of Substituted N–Trimethylammoniobenzamidates. The Hammett Correlation and the Thermodynamics of Protonation", by William H. Beck et al.

Tetrahedron Letters, No. 4, pp. 289–292, 1972, "The Curtius Rearrangement in Aminimides" by Herman P. Benecke et al.

J. Am. Chem. soc., 1982, 104, 2437–2444, "Solid–State and Solution Conformation of Homo Oligo–α–aminoisobutyric acids) from Tripeptide to Pentapeptide: Evidence for a 310 Helix$^{1a}$", by Ettore Benedetti.

J. Am. Chem. Soc. 1984, 106, 8146–8152, Folded and Extended Structures of Homooligopeptides from α,α–Dialkylated Glycines. A Conformational Energy Computation and X–ray Diffraction Study, Ettore Benedetti et al.

"First Crystal Structure Analysis Of A Complete Homo–Oligopeptide Series", by Ettore Benedetti et al., pp. 619–624.

Gaza Chem. Ital. 95, 1965, "Reazione dei diarildiazoalcani–Nota IV. Difenildiazometano e azoici carbonilici", Gian Franco Bettinetti et al.

Nucleosides & Nucelotides, 10(8), 1657–1665, 1991 "Synthesis of N–Aminopyrazinium Analogs of Cytidine and 2'–Deoxycytidine", by Miroslav Bobek et al.

J. Am. Chem. Soc. 1984, 106, 8152–8156, "Folded and Extended Structures of Homooligopeptides from α,α–Dialkylated α–Amino Acids. An infrared Absorption and H Nuclear Magnetic Resonance Study", by Gian Maria Bonora.

Bull. Soc. Chim. Belg., vol. 84/n4/1975, pp. 299–304, "Synthesis of a Homologous Series of Protected Oligopeptides Derived From L–Norvaline" by G.M. Bonora et al.

Tetrahedron vol. 38, No. 24, pp. 3579–3583, 1982, "(–)–Isovaline: Confirmation of its D–(+R)–Configuration by X–Ray Analysis of Its N–Chloroacetyl Derivative", by R. Bosch et al.

Tetrahedron Letters No. 31, pp. 2689–2690, 1976, "Allylic and Benzylic Deamination By Thermal Cleavage of 1–substituted 1,2–Dihydro–2, 4, 6–Triphenylpyridines" by A.J. Boulton et al.

Current Chemotherapy, vol. II, 1213–1216, "Observations on the Antineoplastic Activity of Aminimides", by L. Boutis et al.

Chemistry and Industry, 11Jul. 1970, "Kinetics of reaction between gaseous oxygen and cobalt(II) ammines" by R. Bratchley et al.

Tetrahedron Letters vol. 21, 5059–5060, 1980, "New Cyclic Aminimides Containing Pyrazolone Skeleton", By M. Poje and N. Bregant.

Journal of Chemical and Engineering Data, vol. 12, No. 4, "Preparation of Some New Aminimides", by Melancthon S. Brown.

Biopolymers, vol. 12, 2599–2605 (1973), "An Obligatory α–Helical Amino Acid Residue" by Antony W. Burgess et al.

J. Chem. Soc., 1972, 1071–1076, "Structural Investigations of Ylides. Part I. Crystal and Molecular Structures of Trimethylammoniobenzamidate and Trimethylammonionitramidate: Two Stabilised Nitrogen–Nitrogen Ylides", by A.F. Cameron.

Chemical Communications, No. 14, Jul. 21, 1971, 725–726, "Crystal and Molecular Structures of Two N–Ammonio–amidates", by A.F. Cameron.

Journal of Pharmaceutical Sciences, vol. 75, No. 4, Apr. 1986, 407–409, "2,2'–Phthaloyl–, 2,2'–Isophthaloyl–, and 2,2'–Terephthaloylbis[1,1,1–trimethylhydrazinium] Dihydroxie, Bis(Inner Salts): Synthesis: Partition Coefficients, Toxicity and Effect on Ganglionic Transmission", by Lindley A. Cates.

Chemical Abstracts, vol. 89, 1978, p. 250, Mosquito larvicidal and pupicidal activity of aminimides, by E. Clarke et al.

"Synthesis of 2,2'–Bis–[5(4H)–oxazolones]" by Charles S. Cleaver et al, 1954, vol. 77, pp. 1544–1546.

Meth and Find Exptl Clin Pharmacol 1987: 9(2):101–110, "Pharmacological Properties of Besulpamide, a New Diuretic, in Rats and Dogs", by M. Colombo, et al.

Biochemical and Biophysical Research Communications, vol. 79, No. 1, 1977, The Crystal and Molecular Structure of the Amino Terminal Tetrapeptide of Alamethicin. A Novel $3_{10}$ Helical Conformation.

Newcastle Technical Centre, 1274–1280, Jun. 1969, "Light Scattering by Polydisperse Cylindrical Micelles", by J.M. Corkill et al.

Tetrahedron, vol. 49, No. 15, pp. 3185–3192, 1993, "2–Alkoxycarbonylcycloimmonium Ylides, Efficient 1,4–Dipole Equivalents in the Synthesis of New Conjugated Betaines", by Ana M. Cuadro et al.

Journal of Polymer Science, Part A–1, vol. 6, 363–373 (1968), "Aminimides, IV. Homo–and Copolymerization Studies on Trimethylamine Methacrylimide", by B.M. Culbertson.

Macromolecules, vol. 1, p. 254, May–Jun. 1968, "Aminimides, VII. Homo–and Copolymerization Studies on 1,1–Dimethyl–1–(2–hyroxypropyl)amine–Methacrylimide . . . ", by B.M. Culbertson.

Aminimides, vol. 3, No. 6, Nov.–Dec. 1970, 715–722, "Aminimides, VIII Synthesis and Homo–and Copolymerization Studies of 1,11–Trimethylactrylylhydrazinium Chloride and 1,1,1–Trimethylmethacrylylhydrazinium Chloride", by B.M. Culbertson et al.

Journal of Polymer Science: Part A–1, vol. 6, 2197–2207 (1968), "Aminimides V. Preparation and Polymerization Studies of Trimethylamine–4–Vinylbenzimide", by B.M. Culbertson et al.

Applied Polymer Symposium No. 26, 399–410 1975, "Synthesis and Polymerization Studies of Aminimide Monomers Containing Acetoxyl or Carboxylic Acid Residues", by B.M. Culbertson et al.

J. Org. Chem, USSR 1966, 2, Aminimides cyclic.

Proceedings of the Seventh American Peptide Symposium, Peptides–Synthesis–Structure–Function, pp. 303–306, "Sterically–Hindered Amino Acids, Directors of Peptide Conformation", by N.G. Delaney et al.

Meth and Find Exptl Clin Pharmacol 1987; 9(2):111–119, "Acute, Subacute and Subchronic Toxicity of Besulpamide", by I. Demestre et al.

Tetrahedron vol. 48, No. 23, pp. 4733–4748, 1992, "Asymmetric Synthesis of Unusual Amino Acids: An Efficient Synthesis of Optically Pure Isomers of β–Methylphenylalanine" by Ramalinga Dharanipragada et al.

Inorg. Nucl. Chem. Letters, vol. 10, pp. 233–235, 1974, "Ortho–Metallation Reactions With 1–Benzoyliminopyridinium Betaine", by Shelton A. Dias et al.

J. Chem Soc., 162, 1975, J.C.S. Dalton, "Metal–Ylide Complexes. Part I. Metallation Reactions . . . ", by Shelton A. Dias et al.

Chemical Abstracts, vol. 70, 1969, 264, "Synthesis of 1–alkyl–1, 1–dimethylhydrazinium salts and N–alkyldimethylaminoacetimides and their properties", Kameyama, Eiichi et al.

Meth and Find Exptl Clin Pharmacol 1987; 9(2):121–126, "Pharmacokinetics of Besulpamide in Rats and Dogs", by J. Esteve.

Chemical Abstracts, vol. 115, 1991, p. 44, "Elimination of disturbances of the heart electric stability and arrhythmias with a synthetic analog of acetylcholine" by F.Meerson et al.

Polymer Bulletin 22, 449–454(1989), "Synthesis and reactivity of highly versatile VDMO–VBC copolymers" by Robert C. Fazio et al.

Tetrahedron, vol. 31, pp. 2559–2569, 1975, "N–(6, 7–Methylenedioxy–3–Quinazolinio)Amidates–I Synthesis Spectra and Some Dark Reactions", J. Fetter.

FEBS Letters, Vol. 155, No. 2, "The crystal structure of a 310 helical decapeptide containing α–aminoisobutyric acid" by A.K. Francis.

J. Chem. Soc. Perkin Trans. II 1982, pp. 1235–1239, "The Crystal Structure of the Amino–terminal Pentapeptide of Suzukacillin. Occurrence of a Four–fold Peptide Helix", by Athappilly K. Francis.

Biopolymers, vol. 22, 1499–1505 (1983), "Crystal Structure of Boc–Ala–Aib–Ala–Aib–Aib–Methyl Ester, A Pentapeptide Fragment of the channel–Forming Inonophore Suzukacillin", by A.K. Francis et al.

J. Chem. Research (S), 192–193, 1988, "Photochemistry of Trialkylammonio–N–benzoylimides: Rearrangement and Amide Formation" by Sally Freeman et al.

J. Chem. Research(S), 354–355 1989, "Base–induced Rearrangement of 1,1,1,2–Tetraethyl–2–benzoylhydrazinium Iodide to N–(Dimethylaminomethyl)–N–methylbenzamide" by Sally Freeman et al.

Journal of the American Oil Chemists' Society, vol. 49, "Aminimides XIII Long Chain Aminimides and Isocyanates", by R.E. Freis et al.

J. Heterocyclic Chem., 26, (Sep.–Oct. 1989), 1373–1382, Study of the Structure of Besulpamide, 1-[–Chloro–3–sulfamoylbenzoyl)amino]2,4,6–trimethylpyridinium hydroxide inner salt, and related compounds, using X–ray Crystallography and 'H and $^{13}$C Nuclear Magnetic Resonance Spectroscopy, Jordi Frigola et al.

Chemical Communications, 1968, 917–918, "The Crystal Structure of a Novel Heterocycle containing and Intramolecular Carbon–Nitrogen Hydrogen Bond", by Charles J. Fritchie et al.

J.C.S. Perkins II, 1978, 431, "Basicity of the Carbonyl Group. Part 6, Calorimetric and Specto–metric Study of Complexation of para–substituted N–Ammoniobenz–amidates by Boron Trifluoride", by Jean–Francois Gal et al.

Intra–Science Chemistry Reports, vol. 5, No. 4, 1971, pp. 305–316 "Studies on the Biologically–Active Conformations of Angiotensin" by Garland.

J. Chem. Soc. (C), 1967, 2577–2580, Thermolysis of Trimethylamine–benzimide and Related Compounds: Identification of By–products and their Probable Mechanism of Formation by Martin S. Gibson et al.

Acta Chem. Scand. 9 (1955), No. 9, 1498–1509, "The Reaction of Hydrazine with Cinnamic Acid Derivatives", by W.O. Godtfredsen et al.

Polymer Letters, vol. 2, pp. 1095–1096 (1964), "Thermally Reversible Homopolymer Gel Systems", by Howard Haas et al.

Tetrahedron Letters, No. 26, pp. 1733–1737, 1964, "Beaktionen von Benzol–Derivaten Mit Nitrenen", by Klaus Hafner et al.

Lipids, vol. 20, No. 10 (1985), 685–692, "Hypolipidemic Activity of the Surfactants Aminimides, and Their Effects on Lipid Metabolism of Rodents", by Iris H. Hall.

Int. J. Peptide Protein Res. 21, 1983, 392–405, "Peptides containing dipropylglycine", by Paul M. Hardy et al.

Bull. Soc. Chim. Belg., 65, pp. 291–296, 1956, "Syntheses des isocyanates de vi2nyle et d'isoprpenyle", by R. Hart.

Journal of Fluorine Chemistry, 51, 1991 419–431, "Amine-(polyfluoroalkoxyacyl)imide Surfactants[1]", by Lisa Haywood et al.

"The Chemistry of 2–Alkenyl–2–Oxazolin–5–Ones" by Steven H. Heilmann et al.

Journal of Polymer Science, vol. 22, 3149–3160(1984), "Chemistry of Alkenyl Azlactones. IV. Preparation an Properties of Telechelic Acrylamides Derived from Amine–terminated Oligomers" by Steven M. Heilmann et al.

J. Am. Chem. So., 1982, 104, pp. 2437–2444, Solid–State and Solution Conformation of Homo Oligo (α–aminoisobutyric acids) from Tripeptide to Pentapeptide: Evidence for a $3_{10}$ Helix[1a].

J. Med. Chem. 1991, 34, 1777–1789, "Synthesis, Conformational Properties, and Antibody Recognition of Peptides Containing β–Turn Mimetics Based on α–Alkylproline Derivatives" by Mark G. Hinds.

J. Org. Chem., 24, 1825, vol. 28 (1959), "Alkyl–(alkoxyalkyl–)hydrazones", by John C. Howard et al.

University of Arizona, pp. 797–804, "Design of Drugs Acting at Peptidergic Receptors", by Victor J. Hruby.

Biopolymers, vol. 22, 517–530(1983), "Conformational and Dynamic Considerations in the Design of Peptide Hormone Analogs", by Victor J. Hruby et al.

Die Angewandte Makromolekulare Chemie 11 (1970) 109–124, "Syntheses und Reaktionen von 2–Alkenyloxazolonen" by Von Klaus Hubner et al.

Liebigs Ann. Chem. 1977, 506–527, "Additionen mit Chinolinium–, Isochinolinium–und Phenanthridinium–N--imid", by Rolf Huisgen et al.

Journal of the American Oil Chemists' Society, vol. 55, Feb. 1978, "Properties of 2–Hydroxyethylamine Acylimide Aqueous Solution—Unusual Clouding Phenomenon", Isao Ikeda et al.

Journal of the American Oil Chemists' Society, vol. 53, 1976, "Synthesis of 1,1,1–Tris(2–hydroxyethyl)amine–2–acylimide", Isao Ikeda et al.

Organic Mass Spectrometry, 1971, vol. 5, pp. 61 to 71, "The Mass Spectra of N–Acyliminopyridinium and Isoquinolinium Betaines", by M. Ikeda et al.

The Chemical Society of Japan, No. 3, 1982, "Synthesis, Surfactant Properties and Catalytic Action of Crown Ethers Bearing Aminimide Group", by Seiichi Inokuma et al.

Journal of Polymer Science: Part A: Polymer Chemistry, vol. 25, 1363–1382 1987, "Thermal Decomposition Behavior of Bis–aminimides and Their Application to Polymerization of Epoxide" by Shinzo Inubushi et al.

Journal of Polymer Science: Part A: Polymer Chemistry, vol. 25, 137–150 (1987), "Thermal Decomposition Behavior of Mono–aminimides and Their Application to Polymerization of Epoxide", by Shinzo Inubushi et al.

Journal of Polymer Science, Part A:, Polymer Chemistry, vol. 26, 1779–1789 (1988), "Tough Epoxy Resins Cured with Aminimides", by Shinzo Inubushi et al.

Can. J. Chem., vol. 52, 1974, 3671–3675, "New Route to Cyclic Azomethine Imines", By P.C. Ip et al.

The Journal of Organic Chemistry, Aug. 31, 1966, "Synthesis of N–[1–(1–Substituted 2–oxopropyl)]acrylamides and –methacrylamides. Isolation and some Reactions of Intermediates of the Dakin–West Reaction", by Yosmo Iwakura et al.

Journal of Molecular Structure, 243 (1991) 365–368, "A Multinuclear NMR Study On Some Cyclic Aminimides and Related Compounds", by J. Jazwinski.

Biopolymers, vol. 22, 241–246(1983), "Stabilizing Effects of 2–Methylalaline Residues on β–Turns and α–Helixes", by G. Jung.

Coyright 1981 by Walter de Gruyter Berlin, Structure and Activity of Natural Peptides, Properties of the Membrane Modifying Polypeptide Antibiotics Alamethicin and Trichotoxin A–40, by Gunther Jung.

Journal of the American Oil Chemists' Society, 52, 1975, "Aminimides: II. Antimicrobial Effect of Short Chain Fatty Acid Derivatives", by J.J. Kabara et al.

Chemistry Letters, pp. 413–414, 1976, "Synthesis and Characterization of 1–Imidoyliminopyridinium N–Ylides", by Akikazu Kakehi et al.

Chemical Abstracts, vol. 72, 1970, 45292–45293, "Reactive surfactants. II. Synthesis of 2–acyl–1,1,1–trimethylhydrazinium hydroxide inner salts and their properties", by E. Kameyama et al.

Nippon 1974, No. 9, 1789, "Preparation of Some Properties of (2–Hydroxyalkyl)–dimethylammonium–N–acylimine", by Eiichi Kameyama et al.

Chem. Phar. Bull., vol. 23, 1975, 452–455, "Studies on Ketene and Its Derivatives. LXVIII Reaction of Kiketene with N–Imino–pyridinium, –quinolinium, and –isoquinolium Ylides", Tetsuzo Kato et al.

Gazzetta Chimica Italiana, 117, 1987, 509–511, "The Structure of the Pyridine 1–Benzimide Mono Cation", by Alan R. Katritzky.

Tetrahedron, vol. 36, pp. 679 to 699, "Conversions of Primary Amino Groups Into Other Functionality Mediated by Pyrylium Cations" by Alan R. Katritzky.

J.C.S. Perkin I, 1979, "Heterocycles in Organic Synthesis. Part 17. Conversion of Primary Amines into Bromides and Chlorides", by Alan R. Katritzky et al.

J.C.S. Perkin I, 1979, "Heterocycles in Organic Synthesis. Part 19, Thermolysis of Pyridinium N–Acylimines: a New Preparation of Isocyanates", by Alan R. Katritzky et al.

J.C.S. Perkin I, 1979, "Heterocycles in Organic Synthesis, Part 16, The Conversion of Aliphatic, Aromatic, and Heteroaromatic Primary Amines into Iodides" by Alan R. Katritzky et al.

J.C.S. Perkin I, 1979, "Heterocycles in Organic Synthesis. Part 24. A New Synthesis of NN'–Diarylcarbodi–imides", by Alan R. Katritzky et al.

Angew: Chem. Int. Ed. Engl. 23 420–429, 1984, Pyrylium Mediated Transformations of Primary Amino Groups into Other Functional Groups, by Alan R. Katritzky et al.

J.C.S. Perkin I, 1981, 1495–1500, "Reactions of Pyryliums with Mono–and asym–Di–substituted Hydrazines" by Alan R. Katritzky et al.

Heterocycles, vol. 18, 1982, "Pyrazolo(1,5–c)Pyrimidines from pyrylium Salts and Amidrazones and Pyridine Imidoyl–N–Imides from Imidoyl Chlorides", by Alan R. Katritzky et al.

J. Am. Chem. Soc. 1991, 113, 2275–2283, "Topographic Design of Peptide Neurotransmitters and Hormones on Stable Backbone Templates: Relation of conformation and Dynamics to Bioactivity" by Wieslaw M. Kazmierski et al.

J. Org. Chem., 1981, 46, 2490–2497, Relative Reactivity and Structures of Benzoyltrimethylhydrazine and 1–Benzoyl–2–methylpyrazolidine, by Spencer Knapp.

Journal of Polymer Science: Polymer Chemistry Edition, vol. 21, 3597–3600 1983, "Synthesis of Polymers Containing Pyridinium Ylide and Iminopyridinium Ylide Structure", by S. Kondo et al.

Chem. Berg. 103, 2052–2061 (1970), Umlagerung von quartaren Allyl–, Benzyl–und Propargyl–hydraziniumsalzen, by Karl–Heinz Konig et al.

Tetrahedron, vol. 38, No. 14, pp. 2165–2181, 1982, "Syntheses von 2–Methylalanin–Peptiden, die pH–Abhangigkeit Ihrer $^{13}$C–NMR–Spektren und Eine Neue Methode Zur Auswertung uber CS–Diagramme," by Dieter Leibfritz.

Chemica Scripta, 1978–79, 13, 195–196, "Electron Deficient Heteroaromatic Ammonioamidates, 20[1]; N–(3–Quinazolinio)amidates, 8[1]", by M. Lempert–Sreter, et al.

J. Chem. Soc. Perkin Trans. 1 1983, "Electron Deficient Heteroaromatic Ammonioamides., etc.", by Magda Lempert–Sreter et al.

Tetrahedron, 1960, vol. 11, pp. 39 to 51., "Synthesis of Peptides Derived From Alpha–Methylalnine", by M.T. Leplawy et al.

Helvetica Chimica Acta—vol. 65, Fasc. 1 (1982)–Nr. 18, "18. Azimine. VI. $^{12}$) 1–Alkoxycarbonyl–2,3–dialkyl–und –2,3–diaryl–azimine" by von Christian Leuenberger.

Monatshefte fur Chemie, 120, 749–758 (1989), "1–Amino–2–hydrazinopyrimidin–N–ylides. Unusual Tautomers of 1–Aminopyrimidin–2–hydrazones", by Jurgen Liebscher.

J.C.S. Perkin, Trans 2, 1977, 909–914, "Mono–and Di–protonation Sites in N–Ammonio–amidates: a Specro–scopic Study", by Milica Liler.

J.C.S. Perkins II, 1980, 380, "The Kinetics of Hydrolysis of N–Trimethylammonioacetamide and of Substituted N–Trimethylammoniobenzamides in Concentrated Sulphuric Acid", by Milica Liler et al.

J.C.S. Chem. Comm., 1975, 93–94, "Methylation and Protonation Sites in Some N–Ammonioamidates" by Milica Liler et al.

Tetrahedron Letters No. 30, 2621–2624, 1974, "A convenient Thermal Route to N,N–Dialkylaminoisocyanates", by William J.S. Lockley.

Tetrahedron Letters No. 48, 4263–4266, 1974, "Cyclic Aminimides Containing The pyrazolone Skeleton", by William J.S. Lockley.

Canadian Journal of Chemistry, vol. 50, 1972, "Reaction of Diphenylcyclopropenethione with Pyridinium Imines", by J.W. Lown et al.

Tetrahedron Letters No. 5., 425–428, 1971, "Cycloadditions of Aminoisocyanates to Heterocumulenes", by Walter Lwowski et al.

Supplement II to Circulation Research, vols. XXX and XXXI, Sep. 1972, pp. 143–150, "Angiotensin II—Studies on the Biologically Active Conformation", by Garland R. Marshall, et al.

Plastics Manufacturing., vol. 83, 1975, "Amine imides" by Kanji Matsueda et al.

Liebigs Ann. Chem. 1980 715–724, "Die Kristallstruktur von α(tert-Butyloxycarbonylamino)-isobuttersaure" by Wilfried Mayr et al.

Canadian Journal of Chemistry, vol. 45, 1967, Aminimides. I. "A General Synthesis of Aminimides From Acyl Hydrazides and Their Pyrolysis", by William J. McKillip.

Canadian Journal of Chemistry, vol. 45, 1967, 2619–2622, "Aminimides. II. A one-step synthesis of aminimides from carboxylic acid esters", by William J. McKillip.

Chemical Reviews, 1973, vol. 73, No. 3, pp. 255–281, "The Chemistry of Aminimides", by W.J. McKillip et al.

Chemical Abstracts, vol. 114, 1991, p. 40, "Antiarrhythmic effect of adaptive activation of the vagal system and a new synthetic acetylcholine analog", by F.Z. Meerson.

Journal of Polymer Science: Polymer Chemistry Edition, vol. 21: 1159–1164 1983, Synthesis of Aminimide Monomers and Polymers, Avinash C. Mehta et al.

Structural Biology, 348–350, "Peptidomimetics in the study of opiate peptides", by Dale F. Mierke et al.

Journal of Polymer Science: Part A: Polymer Chemistry, vol. 29, 29–37(1991), "Copolymers of 2–Vinyl–4,4–Dimethylazlactone with Styrene and Ethyl α–Hydroxymethylacrylate" by Jeno Muthiah et al.

Acc. Chem. Res. 1981, 14, pp. 356–362, "Alamethicin, a Transmembrane Channel'" by Ramakrishnan Nagaraj et al.

Journal of the American Chemical Society, 101:1, Jan. 3, 1979, "Stereochemically Constrained Linear Peptides. Conformations of Peptides Containing α–Aminoisobutyric Acid", by R. Nagaraj et al.

Acta Cryst. (1980), B36, 1498–1500, "Structure of a Peptide Oxazolone: 2–(1'–Benzyloxycarbonylamino–1'–methylethyl)–4, 4–dimethyl–5–oxazolone", by C.M.K. Nair et al.

Tetrahedron Letters, vol. 30, No. 49, pp. 6845–6848, 1989, "Asymmetric Synthesis of Unusual Amino Acids: Synthesis of Optically Pure Isomers of α–methyltyrosine", by Ernesto Nicolas.

Journal of Applied Polymer Science, vol. 27, 2361–2368 1982, "Aminimide as Hardener/Curing Promoter for One Part Epoxy Resin Composition", by Hideki Niino et al.

Chem Pharm Bull, vol. 11 (1963), pp. 774–748, "Pyridazine Derivatives IV. The Structures of Aminopyridazines", by Yoshiro Nitta.

Journal of Applied Polymer Science, vol. 27, 2361–2368 (1982), "Aminimide as Hardener/Cruing Promoter for One Part Epoxy Resin Composition", by Hideri Nhno and Saburo Noguchi.

Chem. Pharm. Bull., vol. 11, 9163), "Reaction of N–Aminopyridinium Derivatives. II. The Reactions of 1–(N–Acylalkylamino)pyridinium Salt Derivatives with Cyanide Ion. (A New Synthesis of Primary Amines)", by Tohsihiko Okamoto et al.

Chem. Pharm. Bull., vol. 14(5) 518–523, 1966, "Reaction of N–Aminopyridinium Derivatives.V. Syntheses of 1–(N–Methylacetamido) alkylpyridinium Salts and Their Reaction with Cyanide Ion", by Toshihiko Okamoto et al.

Tetrahedron, vol. 41, No. 12, 2239–2329, 1985, "Heterocyclic Mesomeric Betaines", by W. David Ollis.

J. Am. Chem. Soc., vol. 103, No. 11, 1981, pp. 2948–2955, "Sensitivity of Polypeptide Conformation to Geometry. Theoretical Conformational Analysis of Oligomers of –Aminoisobutyric Acid", by Yvonne Paterson et al.

J. Org. Chem., 1982, 47, 5023–5025, Degradation of Aminimides Obtained from Enamines and (Ehoxycarbonyl)nitrene, by Lucio Pellacani et al.

Journal of Molecular Structure, 86 (1982) 341–347, "Quantum Theory of the Structure and Bonding in Proteins", by David Peters and Jane Peters.

J.C.S. Dalton I, 1978, 1155, "Reactions of 2–Azidopyridine and 1–Pyridinio Ylides with Transition–metal Complexes", by Maddalena Pizzotti.

The Journal of Organic Chemistry, vol. 33, No. 10, Oct. 1968, "Bridgehead Nitrogen Heterocycles. I. A Convenient Synthesis of Pyrazolo[1,5–a]pyridines", by K.T. Potts et al.

J. Chem. Soc., Perkin Trans. 1 1983, 417–421, "Molecular Structure of Boc–Aib–Aib–Phe–Met–NH$_2$ DMSO. A Fragment of a Biologically Active Enkephalin Analogue", by B.V. Venkataram Prasad, et al.

Tetrahedron Letters No. 37, 3249–3252, 1974, "Cyclic Aminimides Containing the 3–oxo–5–Thioxo–1,2,4–Triazolidine Skeleton: Rearrangements of 5–Thiourazole Derivatives", by V.T. Ramakrishnan.

Biochemical and Biophysical Research Communications, pp. 898–904, Hydrophobic Channels in Crystals of an χ–Aminoisobutyric Acid Pentapeptide, by Ch. Pulla Rao.

Biochemical and Biophysical Research Communications, vol. 103, No. 3, 1981, pp. 898–904, "Hydrophobic Channels in Crystals of an x–Aminoisobutyric Acid Pentapepetide", by Ch. Pulla Rao et al.

Biopolymers, vol. 21, 2461–2472 (1982), "Molecular Structure of t–Butyloxycarbonyl–Leu–Aib–Pro–Val–Aib–Methyl Ester, a Fragment of Alamethicin and Suzukacillin: a $3_{10}$–Helical Pentapeptide", by Ch. Pulla Rao et al.

Pages 33–34, "Multiazlactones—Potential Alternatives to Isocyanate and Epoxy Resins" by Jerald K. Rasmussen.

Makromol. Chem., Rapid Commun. 5.67–70 (1984), "Chemistry of Alkenylazlactones, $2^{a)}$ Reaction with thiols", by Jerald K. Rasmussen et al.

J. Heterocyclic Chem., 27, 1041 (1990), "Synthesis of Some N–[Pyridyl(phenyl)carbonylamino]–alkyl–1,2,3,6–tetrahydropyridines", by Kinfe K. Redda.

J. Med. Chem., 1979, vol. 22, No. 9, 1079, "Syntheses of N–Substituted 2(3,4)–Pyridylcarboxylic Acid Hydrazides with Analgesic and Antiinflammatory Activity", by Kinfe Redda et al.

Journal of Pharmaceutical Sciences, vol. 81, No. 5, May 1992, "Synthesis and Pharmacological Evaluation of Some N–[Pyridyl(phenyl)carbonylamino]methyl–1,2,3,6–tetrahydropyridines" by Kinfe K. Redda et al.

Chem. Pharm. Bull. 39 (3) 786–791 1991, "Synthesis and Anti–inflammatory Activities of Some N–[Pyridl(penyl)carbonylamino]–tert–butyl/phenyl–1,2,3,6–tetrahydropyridines" by Kinke K. Redda et al.

Nature, vol. 300, Nov. 1982, pp. 325–330, Articles—"A voltage–gated ion channel model inferred from the crystal structure of alamethicin at 1.5–A resolution", by Robert O. Fox, Jr. & Frederic M. Richards.

Tetrahedron, vol. 49, No. 18, pp. 3767–3780, 1993, "Electrophilic Amination of Pyrimidine–2–thiones–Synthesis of Zwitterionic 2–Aminothiopyrimidinium–N–ylides, Pyrimidine–2–ones and Bicyclic Pyrimidinium Compounds", by Beate Riemer et al.

Acta Cryst. (1983), C39, 894–896, "tert–Butyloxycarbonyl–α–aminoisobutyryl–α–aminoisobutyrate Benzyl Ester, $C_{20}H_{30}N_2O_5$", by Patrick Van Roey et al.

Int. J. Peptide Protein Res. 19, 1982, 499–505, "Crystal and molecular structure of tert.—butyloxycarbonyl–L–hydroxy–prolyl–α–aminoisobutyryl–α–aminoisobutryl–L–phenylalaninol",by Patrick Van Roey et al.

Biopolymers, vol. 32, 407–410 (1992), "Peptidomimetics as Receptors Agonists or Peptidase Inhibitors: A Structural Approach in the Field of Enkephalins, ANP and CCK" by Bernard P. Roques.

Tetrahedron Letters No. 52, pp. 4859–4862, 1976, "Regiospecific Versus Non–Regiospecific Photoinduced Ring–Enlargement of 3–Substituted 1–Iminopyridinium Ylides", by Jacques S. et al.

M.R. Chemistry, vol. 20, 1988, 471–474, "Synthesis and Spectroscopic Studies of 2–(1,1–Dimethylhydrazono)propyl Phosphonates" by Miguel Salazar et al.

The Journal of Organic Chemistry, vol. 35, No. 2, Feb. 1970, The Chemistry of Diazepines. The Photochemical Intramolecular 1,3–Dipolar Cycloaddition of Substituted 1–Ethoxycarbonyliminopyridinium Ylides, Tadashi Sasaki, et al.

Journal of Chemistry, 31, Nov. 1966, 3851–3852, "A Novel Synthesis of 1,5–Diphenylpyrazolone–3", by Henry W. Schiessl et al.

J. Prakt. Chem. [2] 110, 204, 1925, "Polyspirocyclische Komplexe des Palladiums mit Phosphor–Yliden", by Hubert Schmidbauer et al.

Liebigs Ann. Chem. 1982, 1304–1321, "The α–Helical Conformation of the Undecapeptide Boc–L–Ala–[Aib–Ala]$_2$–Glu(OBzl)–Ala–[Aib–Ala]$_2$–OMe: Synthesis, X–Ray Crystal Structure, and Conformation in Solution", by Heribert Schmitt.

Liebigs Ann. chem. 1988, 1025–1031, "Asymmetric Synthesis of Boc–L–Val–(R)–α–MePro–OMe, Boc–L–Val–(R)–Proome, and of Boc–L–Val–(R)–α–MePhe–OMe, Ac–L–Val–(R)–α–MePhe–OMe and Their Analogues. A New Strategy for the Synthesis of Non–Proteinogenic Dipeptides", by Ulrich Schollkopf.

Communications, Dec. 1981, pp. 969–971, Asymmetric Syntheses via Heterocyclic Intermediates; VIII. Enantioselective Synthesis of (R)–α–Methyl–α–amino Acids using L–Valine as Chiral Auxiliary Reagent by Ulrich Schollkopf et al.

Angew. Chem., 90 (1978), Nr. 2, pp. 136–138, "Asymmetrische Syntheses von x–Alkyl–x–aminocarbon–sauren durch Alkylierung von 1–chiral–substituierten 2–Imidazonin–5–onen", by Von Ulrich Schollkopf et al.

Angew Chem. Int. Ed. Engl. 18 (1979), No. 11, Enantioselective Synthesis of α–Methyl–αaminocarboxylic Acids by Alkylation of the Lactim Ether of cyclo–(l–ala–l–Ala), by Ulrich Schollkopf et al.

Angew. Chem. Internat. Edit., vol. 14(1975), No. 8, "Applications of Field Desorption Mass Spectrometry in Inorganic Chemistry: Salts", by H.R. Schulten.

J. Org. Chem USSR, 1977, 13, 885, "Reaction of Acyl Nitrenes with Unsaturated Compounds", by V.P. Semenov et al.

Tetrahedron Letters, vol. 27, No. 52, pp. 6319–1986, "Cyclic Carbalkoxy Aminimides. Synthesis and Thermal Decomposition To Give N, N–Dimethylamino Isocyanate", by Jean–Pierre Senet.

Biophy.J., vol. 64, Apr. 1993, 1017–1028, "The permeation properties of small organic cations in gramicidin A channels", by Sang–Ah Seoh.

J.C.S. Chem. Comm., 1978, pp. 996–997, "The $3_{10}$ Helical Conformation of a Pentapeptide Containing a–Aminoisobutyric Acid (Aib): X–Ray Crystal Structure of Tos–(Aib)$_5$–OMe", by N. Shamala et al.

Biochemical and Biophysical Research Communications, vol. 79, No. 1, 1977, "The Crystal and Molecular Structure Of the Amino Terminal Tetrapeptide of Alamethicin. A Novel 310 Helical Conformation", by N. Shamala et al.

J.C.S. Chem.Comm., 1978, 996–997, "The $3_{10}$ Helical Conformation of a Pentapeptide Containing α–Aminoisobutyric Acid (Aib): X–Ray Crystal Structure of Tos–(Aib)5–OMe" by Narayanaswamy Shamala et al.

I–Pharmacology, vol. 108, 1988, p. 31589, "Regulation of carnitive–dependent metabolism of fatty acids in myocardium under the influence of 3–(2,2,2–tri–methylhydrazinium)propionate" Zh. Shutenko et al.

Chemical Abstracts, vol. 115, 1991, p. 45, "Regulation of the carnitive–dependent metabolism of fatty acids in the rat myocardium", Zh. Shutenko et al.

The Journal of Organic Chemistry, vol. 33, No. 4, Apr. 1968, "Aminimides. VI. Synthesis of Aminimides from Carboxylic Acid Esters, Unsymmetrically Disubstituted Hydrazines, and Epoxides", by R.C. Slagel.

Canadian Journal of Chemistry, vol. 45, 2625, (1967), "Aminimides. III. A convenient synthesis of isopropenyl isocyanate", by Robert C. Slagel et al.

Organic Preparations and Procedures Int. 13(1), 55–58, 1981, "Preparation of 2–Hydroxyethyldimethylamine Acylimides" by Robert J. Small.

The Journal of Organic Chemistry—Notes 851–855, "Reactions of Hydrazines with Esters and Carboxylic Acids" by Richard F. Smith.

J. Org. Chem., vol. 41, No. 9, 1976, 1555–1556, "Reaction of 1,1–Dibenzoyl–2,2–dimethylhydrazine with Methyl p–Toluenesulfonate", by Richard F. Smith.

J. Am. Chem. Cos., 1981, vol. 103, pp. 1493–1501, "Crystal Structures and Conformational Calculations of Fragments of Alamethicin Containing Aminoisobutyric" by G. David Smith.

Chemical Communications, 1965, 120, "The Pyrolsis and Photolysis of Trimethylamine Benzimide", by Richard F. Smith.

J. Org. Chem., vol. 59, No. 14, 1974, "Stevens Rearrangement of Carbamoylaminides" by Richard F. Smith et al.

Chemistry Department of the University of Michigan, Sep. 1959, 1325–1332, vol. 24, "Nitroative Cleavage of N',N'–Dialkylhydrazides and Tertiary Amines", by Peter Smith et al.

Bull. Soc. Chem., France—1969 No. 6, 2175–2179, "No. 382—Syntheses Photochimique de (1–H)–Diazepines-1,2" by Jacques Streith et al.

Chem. Ber. III, 780–790 (1978), "Pyrazolium–Betaine aus 1, 1–Dialkylhydrazinen und Acetylencarbonsaureestern", by Wolfgang Sucrow et al.

Journal of the American Chemical Society, 90:19, Sep. 11, 1968, "Novel Heterocyclic Syntheses from Azomethine Imides. 2–Unsubstituted Diazetidinones", by Ken'ichi Takeuchi, et al.

Chem. Pharm. Bull., vol. 31, 1983, 1378–1381, "1,3–dipolar Cycloaddition Reaction of 1–Methylperimidine 3–Ylides with Dimethyl Accetylenedierboxylate", by Yasumitsu Tamura et al.

J. Heterocyclic Chem., 9, Aug. 1972, 865, "Synthesis of 3–substituted N–Aminopyridinium Salts(I)", by Yasumitsu Tamura et al.

J.C.S. Perkin I, 1973, 2580–2583, "Synthesis and Thermal Reaction of 2,2–Diacyl–N–(1–pyridinio)vinyl–aminides: Formation of Pyrazolo[1,5-a]pyridines and Isoxazoles", by Yasumitsu Tamura et al.

Chem. Pharm.Bull., 19(6)1285–1286 1971, "The Photo Arrangement and Thermolysis of N–Benzoylimino–isoquinolinium and Quinolinium Betaines", by Yasumitsu Tamura et al.

Organic Preparations and Procedures 1(3), 217–219 (1969), "A convenient synthesis of 5–oxazolones. 2–phenyl–5–oxazolone" by Lloyd D. Taylor et al.

Polymer Letters, vol. 7, pp. 597–603(1969), "The Synthesis of Vinyl Peptide Monomers", by L.D. Taylor et al.

Journal of Polymer Science: Part C:Polymer Letters, vol. 24, 287–289 (1986), A Polymer whose Aqueous Solutions Show the Properties of Negative Thixotropy and Thermoreversible Gelation: (Poly–(Trimethylamine p–Vinylbenzimide), by LLoyd D. Taylor et al.

Organic Preparations and Procedures 1(3), 217–219(1969), "A convenient Synthesis of 5–oxazolones. 2–Phenyl–5–oxazolone", by L.D. Taylor et al.

Makromol Chem., Rapid Commun. 3, 779–782(1982), "Synthesis of Poly(4,4–dimethyl–2–vinyl–5–oxazolone) an Interesting Material for Preparing Polymeric Agents", by Lloyd D. Taylor et al.

Polymer Letters, vol. 9, pp. 187–190(1971), "Synthesis and Polymerization of 2–vinyl–4,4–Dimethyl–5–Oxazolone" by L.D. Taylor et al.

Rubber Chem. Technology, 53, 1980, "Halogen–containing Aminimide Compounds as Tire Cord Adhesives", by P.E. Throckmorton et al.

Eur. J. Med. Chem.—Chem. Ther. 1982–17, N. 3, pp. 265–270, "Aminimides ethyleniques a action vasodilatatrice peripherique", by Mohamed Tichniouin et al.

Eur. J. Med. Chem., 1982, 17, No. 3, pp. 265–270, "Aminimide ethyleniques a action vasodilatatrice peripherique", by M. Tichniovin et al.

J. Chem. Soc. Perkin Trans. 1988, "Reactions of Some 1,3–Diaminonucleophiles with Azlactones" by Ahmad M. Tikdari et al.

Int. J. Peptide Protein Res. 22, 1983, 603–610, "Bioorganic stereochemistry", by Claudio Toniolo et al.

Biopolymers, vol. 22, 205–215 (1983), Preferred Conformations of Peptides Containing α,α–Disubstituted α–Amino Acids, by Claudio Toniolo et al.

Bull Chem. Soc. Japan, 1980, 53, 1149, "Reaction of Ethyl Aziodoformate with Morpholines", by Teruko Tshuchida et al.

J. Chem. Soc., Chem Commun., 1982, 875–876, "Evidence for Amide Resonance observed in Cyclic N–Ammonio–imitates by X–Ray Photoelectron Spectroscopy", by Shinji Tsuchiya.

J. Chem. Soc. Perkin Trans. 11, 1993, "On the Nature of Nitrogen–Nitrogen Bonding in Cyclic Aminimides", by Shinji Tsuchiya.

Chem. Pharm. Bull. 31(12)4568–4572 1983, "Thermal Rearrangements of Cyclic Amine Ylides. III.[1)] Intramolecular Cyclization of 2–Ethynylpyridine N–Imides to 3–Azaindolizine Derivatives", by Takashi Tsuchiya et al.

J. Org. Chem., vol. 44, No. 16, 1979, 2850–2855, "On the Bond Character of N–Containing Ylides", by Shinji Tsuchiya et al.

Chem. Pharm. Bull., 30(10)3757, 1982, "Studies on Diazepines. XVIII. Photochemical Synthesis of 3H–1,3–Benzodiazepines from Quinoline N–Acylimides", by Takashi Tsuchiya et al.

Bull Chem. Soc. Japan, 1983, 2073, "Double Cycloaddition Reaction of Imidazolium Methylides. Intermolecular 1,3–Dipolar and Intramolecular Diels–Alder Cycloaddition Reactions", by Otohiko Tsuge et al.

Biopolymers, vol. 20, 1123–1136, "X–Pro Peptides: Solution and Solid–State Conformation of Benzyloxycarbonyl–(Aib–Pro)$_2$–methyl Ester, a Type I β–Turn", by Y.V. Venkatachalapathi et al.

Journal of Chemistry, 1966, vol. 31, 1704–1707, "Cyclic Aminimides", by William S. Wadsworth, Jr.

Journal American Chemical Society, vol. 82, 1960, 5718–5721, "The Rearrangement of 1,1–Dimethyl–1–p–nitrobenzylamine–2–acetamide", by S. Wawzonek.

Journal of Chemistry, 28, 1963, vol. 28, 2376–2377, The Resolution of 1–Ethyl–1–methyl–1–p–nitrobenzylamine–2–acetamide, by S. Wawzonek et al.

J. Org. Chem., Sep. 1965, 3031–3033, "The Rearrangement of 1–Methyl–1–acetylimide–2–phenylpyrrolidine", by S. Wawzonek et al.

Organic Preparations and Procedures Int. 8(5), 215–217 (1976), "Electrolytic Preparation of bis–Dimethyl–2–Hydroxypropylamineazobenzimides", by S. Wawzonek et al.

J. Med. Chem., vol. 9, 852–857, "Central Nervous System Depressants. L. 1–Aminoalkyl–3–aryl Derivatives of 2–Imidazolidinone, 2–Imidazolidinethione, and Tetrahydro–2(1H)–pyrimidinone", by William B. Wright et al.

J. Med. Chem., 1982, 25, 720–723, "Synthesis of N–[(Substituted–phenyl)carbonyl]–1,2,3,6–tetrahydropyridines with Analgesic and Hyperglycemic Activity", by Jupita M. Yeung.

J. Med. Chem, 1987, 30, 104–108, "Synthesis of N–(3, 6–Dihydro–1(2H)–pyridinyl)benzamides with Hyperglycemic–Hypoglycemic Actvity", by Jupita M. Yeung et al.

J. Med. Chem. 1982, 25, 191–195, "Synthesis of N–(Carbonylamino)–1,2,3,6–tetrahydropyridines with Analgesic, Antiinflammatory, and Hyperglycemic Activity", by Jupita M. Yeung et al.

Zuckerman, "Identification of highest affinity ligands by affinity selection from equimolar peptide mixtures generated by robotic synthesis, " Proc. Nat. Acad Sci, USA, vol. 89, pp. 4505–4509, May 1992.

5,766,481

METHOD FOR RAPID PURIFICATION, ANALYSIS AND CHARACTERIZATIONS OF COLLECTIONS OF CHEMICAL COMPOUNDS

This is a continuation of application Ser. No. 08/418,233, filed Apr. 6, 1995, now abandoned.

FIELD OF THE INVENTION

The present invention relates generally to methods to manage the purification of a large number of closely related chemical compounds. More particularly the invention relates to the separation of mixtures which were deliberately created from a set of compounds with distinct chromatographic retention times, distinct molecular weights, or other distinguishing features. In a preferred embodiment, a set of n compounds of distinct chromatographic retention times are combined, and then separated in a single chromatographic run, allowing a savings of time relative to the alternative of making n chromatographic runs. The present invention further relates to methods for separating compounds with at least one distinguishing feature by separations other than chromatography.

BACKGROUND OF THE INVENTION

Currently, there are many general methods of purifying synthetic compounds. These methods, which involve purification of a single target compound from multiple impurities, are undesirable for any multiple unit synthesis because the chromatography of large numbers of compounds are difficult to chromatograph in series is very time-consuming and inefficient. This problem is multiplied in a many step synthesis; the requirement of purifying after each step consumes much time.

One example of a conventional technique for simultaneously synthesizing up to 36 individual peptides and thereafter screening said peptides is disclosed in an article by R. N. Zuckerman et al. entitled "Identification of highest-affinity ligands by affinity selection from equimolar peptide mixtures generated by robotic synthesis," Proc. Nat. Acad. Sci., USA, Vol. 89, pp. 4505–09, May 1992.

For purification of an array, or a large number of compounds, the prior art teaches a repetitive method of chromatographing individual compounds. This constitutes a full cycle of synthesis, work-up, and purification for each molecule. While parallel synthesis has been a challenging issue, it is logistically far less complex and time consuming than parallel work-up and purification.

In general, there are several drawbacks with the teachings of conventional methods used by the prior art. In multistep procedures, there is a complexity not involved in single-step procedures, such that there is a greater possibility of error. Additionally, multistep procedures take more time and may use more reagents, and thus are more expensive. Further, the performance of these multiple chromatograms requires large amounts of solvent and time. The repetitive use and wear of columns and packings and subsequent loss of resolution is an additional consideration that could be remedied by consolidation of individual steps.

Therefore, it would be desirable to conduct chemical separations and purifications in a more efficient manner. The present invention provides various solutions to this problem.

SUMMARY OF THE INVENTION

The present invention is based, in part, on the surprising discovery that concurrent coincidental chromatography of desired compounds is a practical, useful method for adequately purifying impure materials. The inventors observed that retention times of similar, but not identical, compounds possess baseline resolution or near-baseline resolution in HPLC chromatography. The present inventors also unexpectedly observed that a mixture of such crude individual compounds provided pure components upon simultaneous preparative chromatographic processing.

It is an object of the present invention to provide a method by which time, labor and expense is saved by combination of crude compounds for simultaneous purification.

Another object is to provide a method by which time, labor and expense is saved by combination of crude compounds and/or reaction mixtures for workup and simultaneous purification.

Another object is to a method by which time, labor and expense is saved by a combination of crude mixtures, or even reactants for reaction, quenching, workup and simultaneous purification.

Yet another object of the present invention is to enable the synthesis of compounds in a large array format, previously thought to be impractical due to the presence of impurities, for the express purpose of generating large libraries for screening or other use.

Many other advantages are realized over the prior art with the present invention, for example, the practical capability for performing non-quantitative, average-yielding reactions in large numbers, due to the fact that now large numbers of compounds may be purified in parallel. Thus, separations which require only one step can be conducted with a significant savings in time. The current method teaches simultaneous chromatography of created mixtures and allows the processing of a much larger number of compounds with the same equipment and unit operations.

The present invention may be more fully understood by reference to the following detailed description, examples of specific embodiments and appended figures which are offered for purposes of illustration only and not by way of limitation.

DETAILED DESCRIPTION OF THE INVENTION

Definitions

Figure 1A:
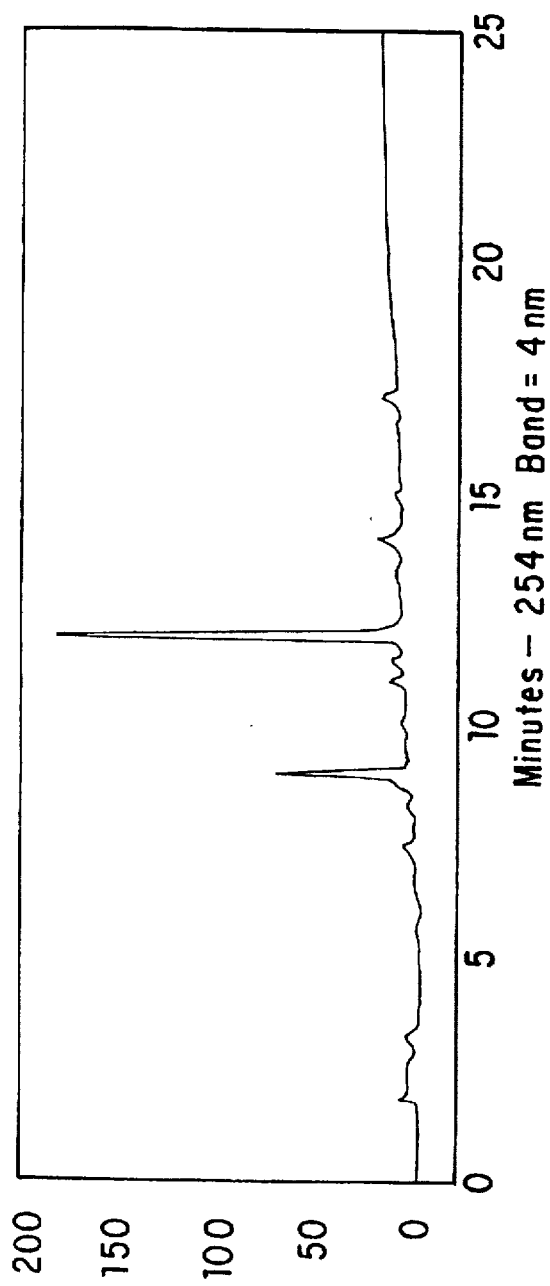
FIG. 1 is a stacked composite of individual chromatograms of Compounds A–E as synthesized, prior to combination and purification.
Figure 1B:
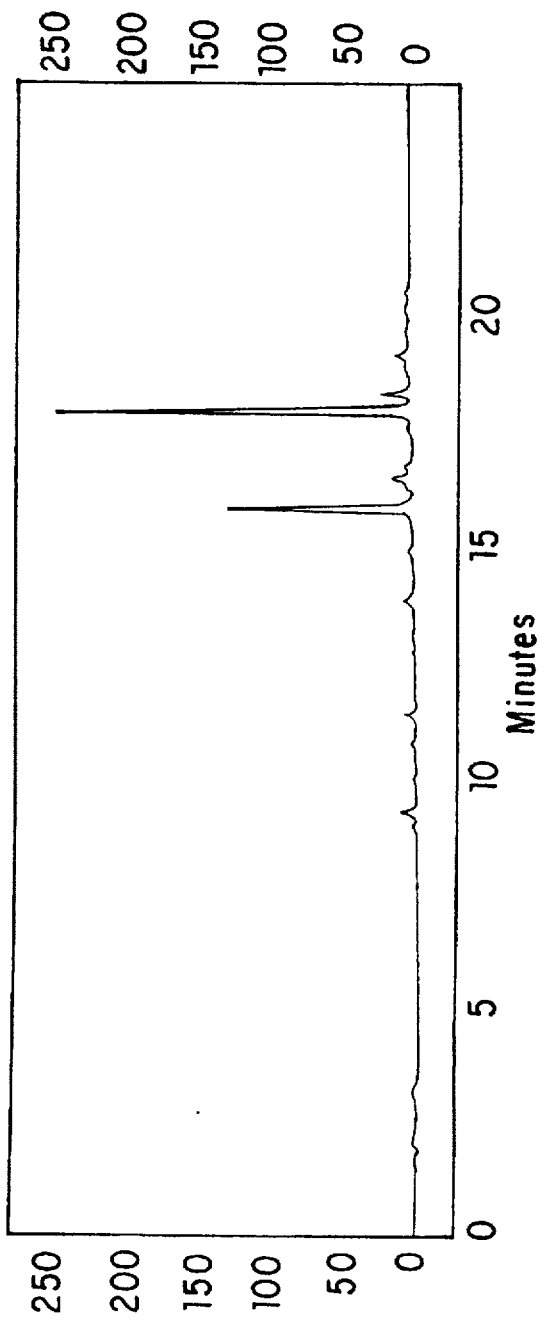
Figure 1C:
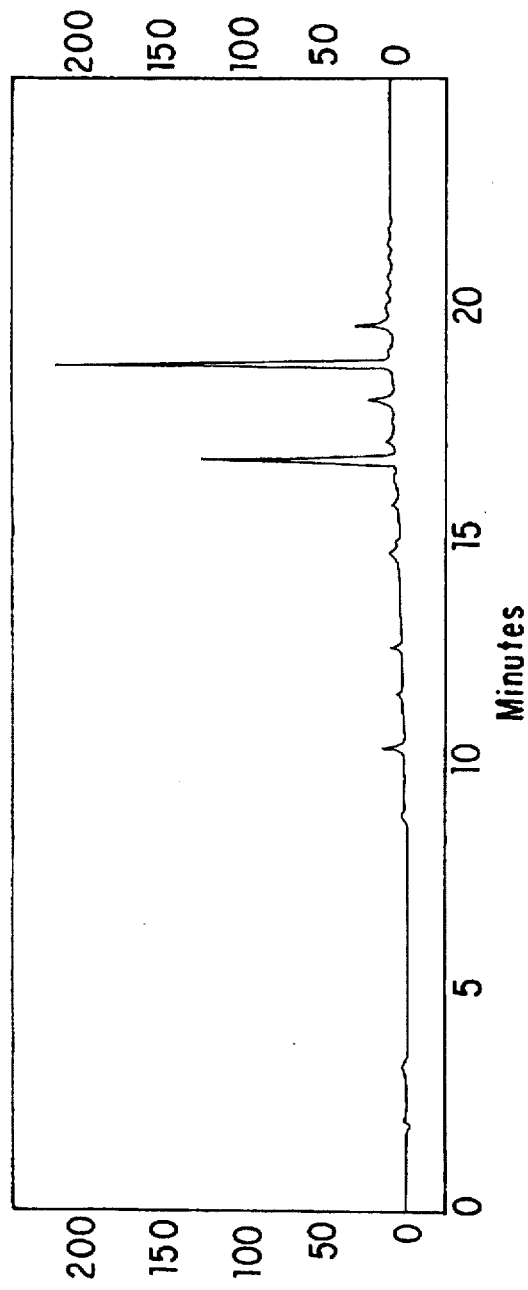
Figure 1D:
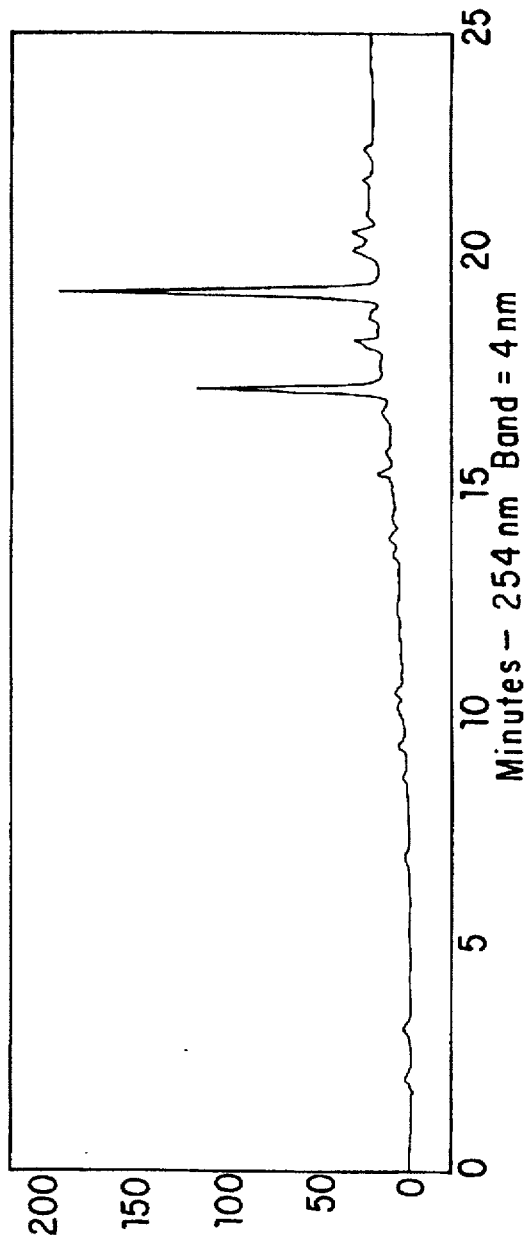
Figure 1E:
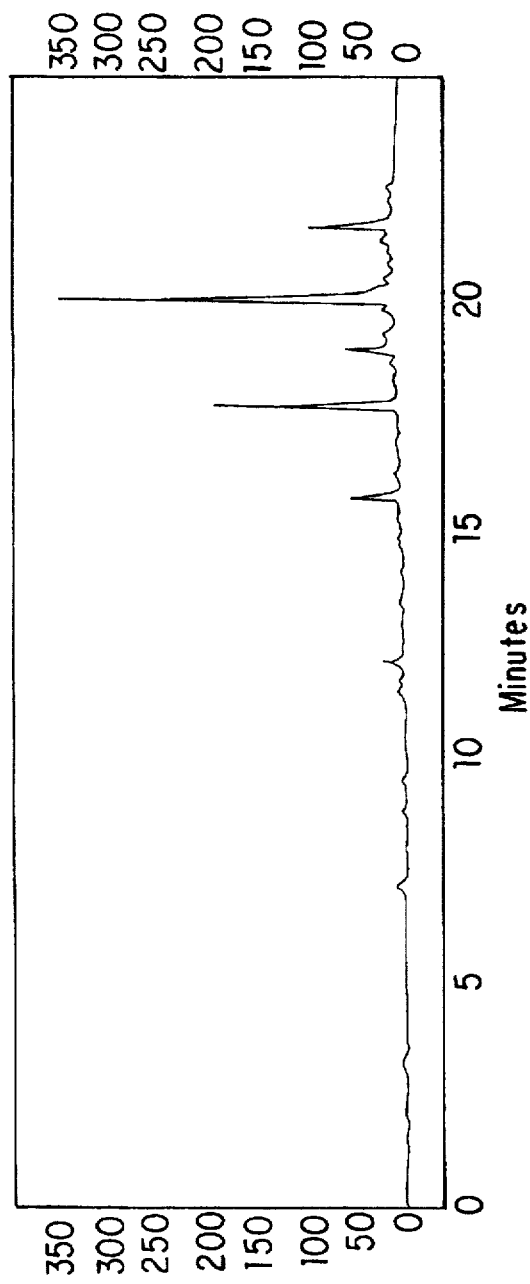

The following terms are used in the present invention to have the meanings set forth below:

"HPLC" encompasses "high performance liquid chromatography".

"Target molecule" refers to a molecule which is intended to be manipulated for the purposes of separation and/or purification. The target molecule, by definition, has no impurities.

"Molecule of interest" refers to a target molecule in a phase which, prior to the application of a purification procedure, comprises both individual target molecules and at least one impurity molecule.

"Set of molecules" is a collection of related or unrelated molecules grouped for the purpose of eased manipulation, but not combined. Within a set of molecules, the user of the process defines which molecules are target molecules.

"Mixture" encompasses a set of molecules that has been combined deliberately for the sole purpose of expediting a unit operation or a chemical transformation.

"Purification" encompasses the eliminating of undesired contaminants and the recovery of desired material in an acceptable level of homogeneity.

"Unit operation" encompasses any manipulation on a set of molecules as a whole, for example screening, work-up or purification.

"Selection parameter" refers to a physical property that is distinct for all target molecules in a set of molecules. One example of a selection parameter can be retention time in HPLC.

"Binding capability" refers to the capacity of a molecule or support to interact in a non-covalent fashion with a specified or unspecified ligand in a thermodynamically-favored process.

"Compatible molecules" means molecules that do not chemically react with one another to form distinct chemical compounds.

Method for Resolution of Molecules

According to one embodiment, the invention comprises a method for the resolution of molecules comprising four steps. First, one or more selection parameters are determined for each member of a set of molecules. A selection parameter could be retention time on HPLC. In this case, the HPLC retention time of each member of the set would be determined analytically or experimentally. Typically, for conventional chromatography equipment, analytical retention times with 15 to 90 seconds difference are preferable and the total operating window can be in the range of 15 to 150 minutes.

Second, the molecules are selected on the basis of chemical compatibility and difference in at least one selection parameter. Chemical compatibility requires that selected molecules not react with one another to form distinct compounds. Difference in selection parameters requires that the selected molecules be distinguishable by experimental methods within the ability of one of ordinary skill in the art. For example, if HPLC retention time were the selection parameter, then the selection process requires each selected target molecule have a distinct HPLC retention time.

Third, the selected molecules of interest would be combined together in any suitable manner, such as by simple mixing.

Fourth, the molecules of interest would be fractionated, such that the impurity level in the molecules of interest is lowered as a result of application of the method. The level of purity of a molecule of interest is somewhat arbitrary and dependent the particular application. Typically purities for one or more of these compounds of about 65% or more are required, and purities greater than 80–90% are often desired. Use of this invention can easily achieve these purities.

This embodiment of the present invention is based on the discovery that, while it is counterintuitive to ever decrease the purity of a molecule in the course of purification, it is convenient to combine, then simultaneously purify, easily separable compounds. Therefore, combining compatible, crude molecules of interest, then chromatographing all of them simultaneously results in a substantial savings in time and material.

The selection of mixtures for the present method of purification via reversible absorptive interactions with the surface of a chromatographic stationary phase is based on knowing the retention time (RT) of every molecule to be purified in a given chromatographic system. The retention times can be sorted by time and combined so as to effect the an efficient throughput for the purification of the set of molecules. A molecule of interest can therefore be combined with other molecules of interest in the set under a given set of selection parameters. Examples of selection parameters can be chromatographic column load, minimum retention time difference, amount of a given molecule, and the maximum underlying impurity allowed to co-elute with a molecule of interest. L. R. Snyder and J. J. Kirkland, *Introduction to Modern Liquid Chromatography*, 1st ed., Wiley-Interscience, New York, 1974.

For example, each molecule of interest can be associated with a given chromatographic peak at a given retention time. Each time a new molecule of interest is proposed to be mixed with another molecule of interest or with a sub-set of the set of molecules to afford a new mixture, the following must be applied:

1. The selection parameter of the new molecule of interest must be compared to the selection parameters of the other molecules of interest already in the sub-set. There must not be a match.

2. The selection parameter of the new molecule of interest must be compared to the selection parameters of the impurity molecules within the all the molecules of interest. There should not be a match. However, if the purity of a molecule of interest after the purification is acceptable, there may be a match in selection parameter of an impurity molecule with the selection parameter of a target molecule.

Preferred Embodiment: HPLC Separation

In a preferred embodiment, between 4 and 12 molecules are selected such that they have discrete retention times in an HPLC and are mixed. The mixture is chromatographed on the HPLC and those fractions not containing one of the molecules of interest are discarded. The molecules of interest are collected and resorted according to a prearranged algorithm in a suitable receptacle or tray, preferably a 96-well plate.

Highly Preferred Embodiment: HPLC Separation

In a highly preferred embodiment, one has a method for time resolution of molecules of interest comprising six steps. First, one determines the retention time on an HPLC instrument for each molecule in a set of molecules. Second, one selects a compatible grouping of molecules to form a set of molecules by optimizing on the basis of retention time, resolvability, and column parameters. Third, one forms a mixture of the molecules of interest. Fourth, one chromatographs the mixture on the HPLC to provide separation and purification of the molecules of interest. Fifth, one collects the fractions containing the molecules of interest. Sixth, one verifies analytically the identity of each fraction.

In an additional embodiment, the set of molecules may be screened following the resolving step to determine which molecules in the set participate in a particular reaction. The method comprises the steps of selecting a group of molecules of interest that are sufficiently dissimilar to provide differing binding capabilities to form a set; forming a mixture of molecules of interest from the set; analyzing the mixture to determine the amounts of the molecules of interest; screening the mixture for a desired interaction which depletes one or more molecules of interest from the mixture; and re-analyzing the resultant mixture of molecules that did not bind to determine the molecule of interest participating in the desired reaction. The selection parameters chosen for the molecules of interest should be sufficiently distinct to enable the amounts of such molecules to be experimentally determined from the mixture. Preferably, the analyzing and re-analyzing steps are conducted on a HPLC column, and the molecules of interest have different retention times.

EXAMPLES

In order to more fully illustrate the nature of the invention and the manner of practicing the same, the following examples are provided, which are not to be construed as limiting the remainder of the disclosure or the scope of the invention in any way whatsoever.

According to the present invention, a purification of five molecules of interest was done. The compounds, 4-benzylidene-1-(2-hydroxyethyl)-2-phenyl-5(4H)-imidazolone (denoted A), 4-(3-methoxybenzylidene)-1-phenylmethyl-2-phenyl-5(4H)-imidazolone (denoted B), 4-(3-methoxybenzylidene)-1-(2-(3-methylphenyl)ethyl)-2-phenyl-5(4H)-imidazolone (denoted C), 4-(3-chlorobenzylidene)-1-(2-methylpropyl)-2-phenyl-5(4H)-imidazolone (denoted D) and 1-(2-methylpropyl)-4-(4-phenylbenzylidene)-2-phenyl-5(4H)-imadazolone (denoted E) were synthesized by thermal rearrangement from the corresponding arylidene diamides, which were in turn derived from the sequential reaction of an aryl aldehyde with 2-phenyl-(4H)-oxazol-5-one, followed by ring opening with the corresponding amine. The molecular structure of the compounds are illustrated below. These five molecules are the target molecules of this example.

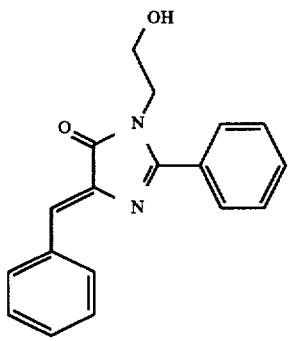

A

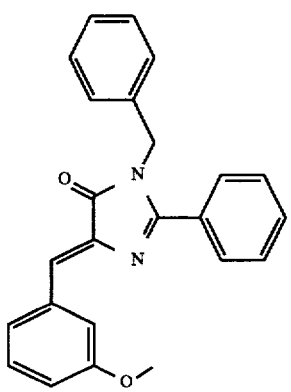

B

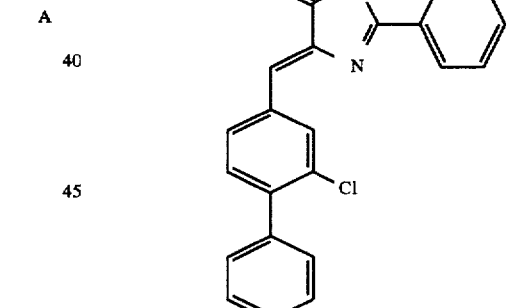

C

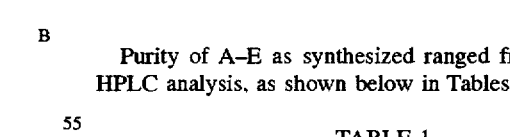

D

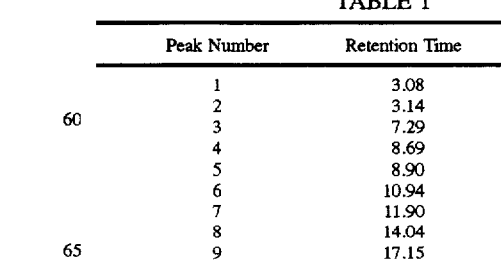

E

Purity of A–E as synthesized ranged from 35–57% by HPLC analysis, as shown below in Tables 1–5.

TABLE 1

| Peak Number | Retention Time | Area Percent |
| --- | --- | --- |
| 1 | 3.08 | 1.30 |
| 2 | 3.14 | 2.18 |
| 3 | 7.29 | 3.17 |
| 4 | 8.69 | 3.49 |
| 5 | 8.90 | 22.41 |
| 6 | 10.94 | 2.89 |
| 7 | 11.90 | 56.80 |
| 8 | 14.04 | 5.14 |
| 9 | 17.15 | 2.63 |

TABLE 2

| Peak Number | Retention Time | Area Percent |
|---|---|---|
| 1 | 3.21 | 0.85 |
| 2 | 9.27 | 2.03 |
| 3 | 9.99 | 0.48 |
| 4 | 10.77 | 0.78 |
| 5 | 11.41 | 1.45 |
| 6 | 12.25 | 0.37 |
| 7 | 12.85 | 0.37 |
| 8 | 13.15 | 0.39 |
| 9 | 13.87 | 1.68 |
| 10 | 14.06 | 0.35 |
| 11 | 14.91 | 1.16 |
| 12 | 15.86 | 26.81 |
| 13 | 16.38 | 1.26 |
| 14 | 16.52 | 2.93 |
| 15 | 16.79 | 0.96 |
| 16 | 17.0 | 0.81 |
| 17 | 17.98 | 48.82 |
| 18 | 18.38 | 3.78 |
| 19 | 18.96 | 1.04 |
| 20 | 19.14 | 2.67 |
| 21 | 19.74 | 0.61 |
| 22 | 20.54 | 0.41 |

TABLE 3

| Peak Number | Retention Time | Area Percent |
|---|---|---|
| 1 | 9.94 | 0.51 |
| 2 | 10.33 | 2.87 |
| 3 | 11.51 | 0.86 |
| 4 | 12.55 | 1.79 |
| 5 | 14.69 | 1.96 |
| 6 | 14.95 | 0.64 |
| 7 | 15.75 | 1.19 |
| 8 | 16.37 | 0.62 |
| 9 | 16.70 | 26.53 |
| 10 | 17.04 | 0.51 |
| 11 | 17.18 | 1.94 |
| 12 | 17.57 | 0.49 |
| 13 | 18.05 | 4.03 |
| 14 | 18.27 | 0.42 |
| 15 | 18.60 | 0.46 |
| 16 | 18.83 | 44.64 |
| 17 | 19.11 | 0.98 |
| 18 | 19.72 | 5.02 |
| 19 | 19.95 | 1.05 |
| 20 | 20.13 | 1.56 |
| 21 | 20.33 | 1.00 |
| 22 | 20.76 | 0.55 |
| 23 | 21.49 | 0.40 |

TABLE 4

| Peak Number | Retention Time | Area Percent |
|---|---|---|
| 1 | 3.08 | 0.53 |
| 2 | 3.14 | 1.50 |
| 3 | 10.14 | 2.03 |
| 4 | 14.29 | 1.67 |
| 5 | 15.30 | 2.82 |
| 6 | 17.13 | 28.75 |
| 7 | 18.13 | 4.74 |
| 8 | 18.72 | 3.42 |
| 9 | 19.22 | 49.81 |
| 10 | 20.12 | 2.80 |
| 11 | 20.54 | 1.92 |

TABLE 5

| Peak Number | Retention Time | Area Percent |
|---|---|---|
| 1 | 3.20 | 0.64 |
| 2 | 7.13 | 1.31 |
| 3 | 9.52 | 0.43 |
| 4 | 11.51 | 1.01 |
| 5 | 11.71 | 0.74 |
| 6 | 12.15 | 2.36 |
| 7 | 12.39 | 0.25 |
| 8 | 12.74 | 0.18 |
| 9 | 13.37 | 0.20 |
| 10 | 14.14 | 0.40 |
| 11 | 14.68 | 0.36 |
| 12 | 14.84 | 0.48 |
| 13 | 15.15 | 0.48 |
| 14 | 15.32 | 0.80 |
| 15 | 15.77 | 5.81 |
| 16 | 16.12 | 0.28 |
| 17 | 16.31 | 0.83 |
| 18 | 16.84 | 0.17 |
| 19 | 17.03 | 0.49 |
| 20 | 17.43 | 0.29 |
| 21 | 17.82 | 19.18 |
| 22 | 18.20 | 0.45 |
| 23 | 18.41 | 0.51 |
| 24 | 18.79 | 1.03 |
| 25 | 19.09 | 5.46 |
| 26 | 19.26 | 1.06 |
| 27 | 19.40 | 1.24 |
| 28 | 19.57 | 0.27 |
| 29 | 19.93 | 1.23 |
| 30 | 20.19 | 35.04 |
| 31 | 20.34 | 2.63 |
| 32 | 20.64 | 1.13 |
| 33 | 21.01 | 0.72 |
| 34 | 21.27 | 0.48 |
| 35 | 21.45 | 0.91 |
| 36 | 21.56 | 0.88 |
| 37 | 21.80 | 8.71 |
| 38 | 22.34 | 0.70 |
| 39 | 22.66 | 0.86 |

A 20 mg sample of each crude mixture was combined in a holder of appropriate size and the five compounds were mixed.

This mixture was applied to a Zorbax ODS-SB RPC-18 column (25×250 mm) and eluted with a 25–100% acetonitrile-1% trifluoroacetic acid (TFA):water gradient. Only those fractions corresponding to known HPLC retention times from previous analysis were collected. The order of elution was A, B, C, D, then E at respective retention times of 25.7, 41.1, 43.1, 44.2 and 46.9 minutes. This is shown in Table 6.

TABLE 6

| Peak No. | Time | Type | Height (μV) | Area (μV-sec) | Area |
|---|---|---|---|---|---|
| 1 | 25.685 | N1 | 282531 | 23004896 | 19.798 |
| 2 | 27.640 | N2 | 4484 | 97192 | 0.083 |
| 3 | 28.028 | N3 | 4662 | 104349 | 0.089 |
| 4 | 41.126 | N | 363074 | 25180404 | 21.670 |
| 5 | 43.088 | N1 | 367402 | 23956860 | 20.617 |
| 6 | 44.191 | N2 | 372506 | 22182110 | 19.090 |
| 7 | 46.871 | N3 | 384929 | 21669772 | 18.649 |
| Total Area | | | | 116195583 | 99.996 |

Re-analysis of the separated compounds revealed purities of 85–97% by HPLC analysis and the identity was confirmed by mass spectrometry. This is shown in Tables 7–11.

TABLE 7

| Peak Number | Retention Time | Area Percent |
| --- | --- | --- |
| 1 | 2.75 | 0.00 |
| 2 | 11.35 | 1.41 |
| 3 | 11.91 | 95.37 |
| 4 | 12.36 | 3.21 |

TABLE 8

| Peak Number | Retention Time | Area Percent |
| --- | --- | --- |
| 1 | 2.76 | 0.00 |
| 2 | 15.70 | 1.05 |
| 3 | 17.49 | 0.99 |
| 4 | 17.90 | 96.77 |
| 5 | 18.29 | 1.19 |

TABLE 9

| Peak Number | Retention Time | Area Percent |
| --- | --- | --- |
| 1 | 2.98 | 0.00 |
| 2 | 16.57 | 0.97 |
| 3 | 17.91 | 0.48 |
| 4 | 18.78 | 95.32 |
| 5 | 19.05 | 3.23 |

TABLE 10

| Peak Number | Retention Time | Area Percent |
| --- | --- | --- |
| 1 | 2.72 | 0.00 |
| 2 | 15.64 | 1.33 |
| 3 | 17.10 | 0.55 |
| 4 | 18.79 | 1.56 |
| 5 | 19.19 | 84.50 |
| 6 | 19.37 | 4.60 |
| 7 | 19.70 | 7.47 |

TABLE 11

| Peak Number | Retention Time | Area Percent |
| --- | --- | --- |
| 1 | 2.71 | 0.00 |
| 2 | 17.71 | 1.51 |
| 3 | 19.91 | 2.66 |
| 4 | 20.18 | 87.89 |
| 5 | 20.41 | 5.13 |
| 6 | 20.62 | 2.81 |

Figure 2:
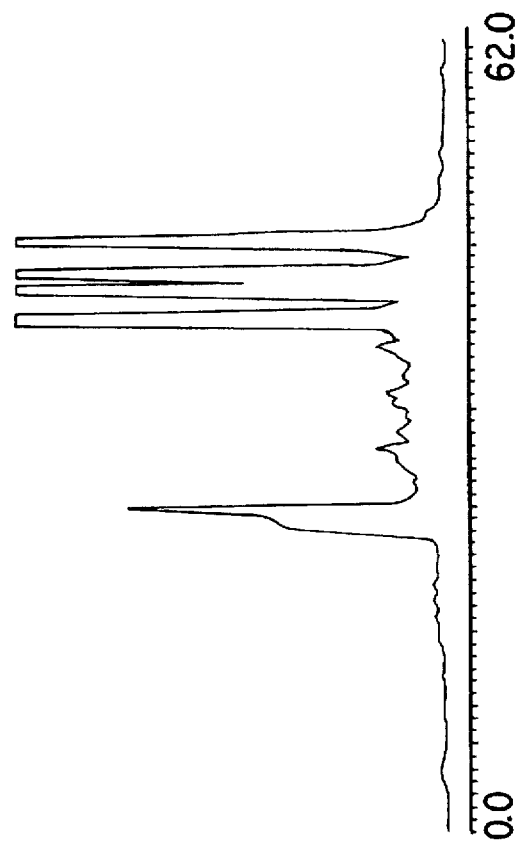
FIG. 2 is a preparative HPLC chromatogram of equimolar mixture of Compounds A–E.
Figure 3A:
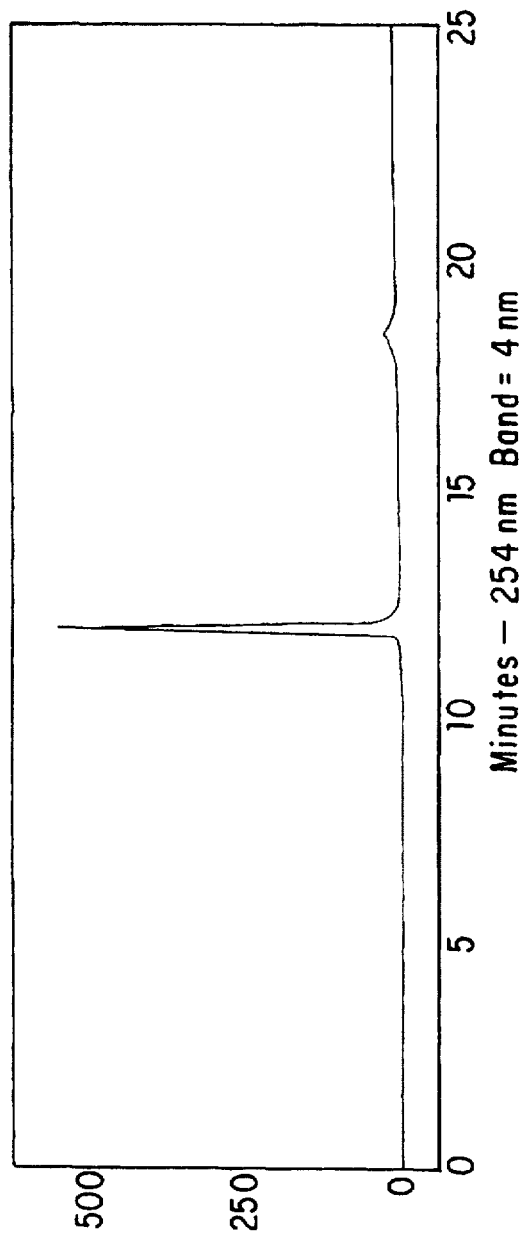
FIG. 3 is a stacked composite of individual chromatograms of Compounds A–E after simultaneous chromatography.
Figure 3B:
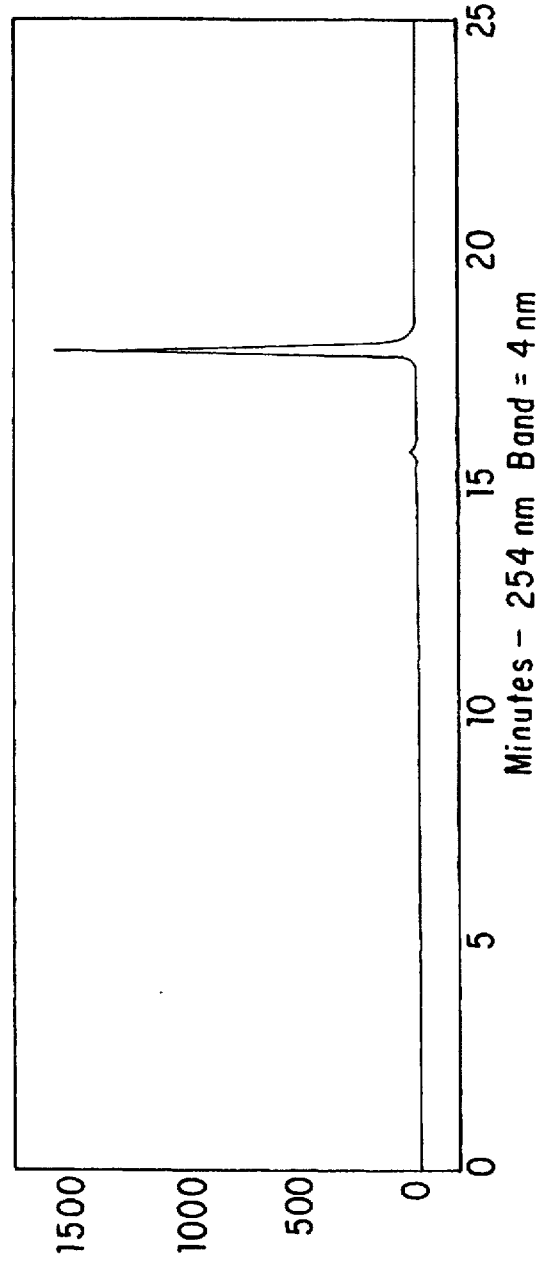
Figure 3C:
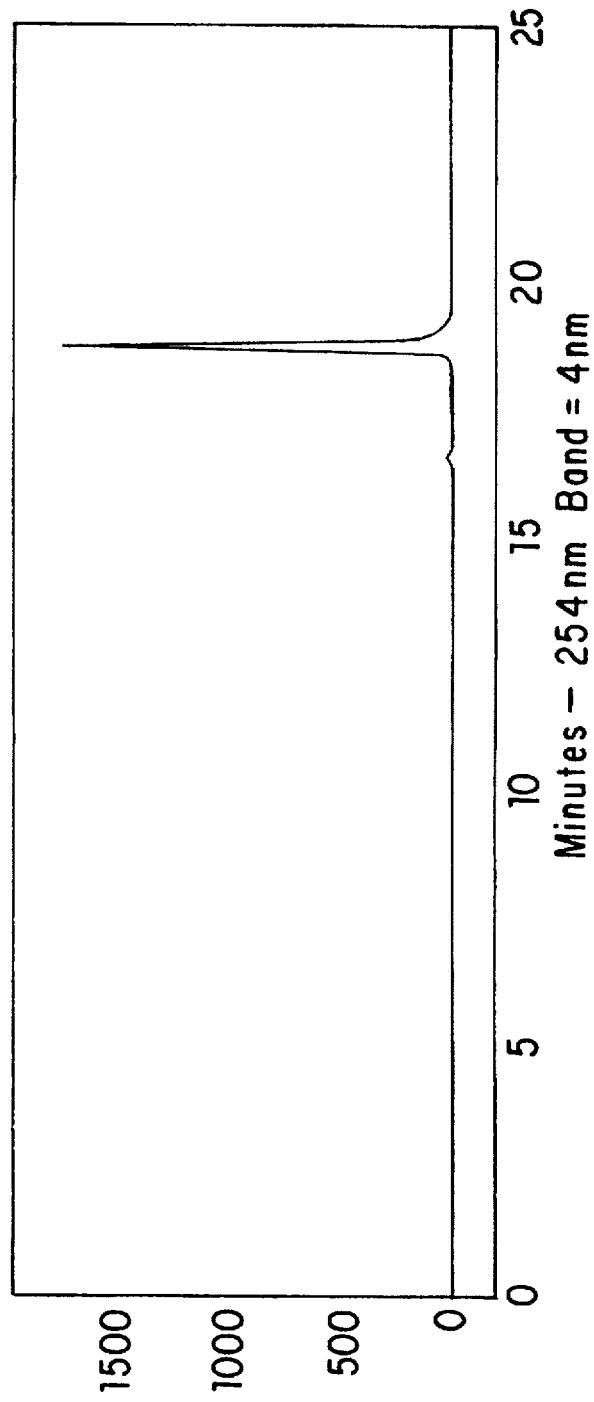
Figure 3D:
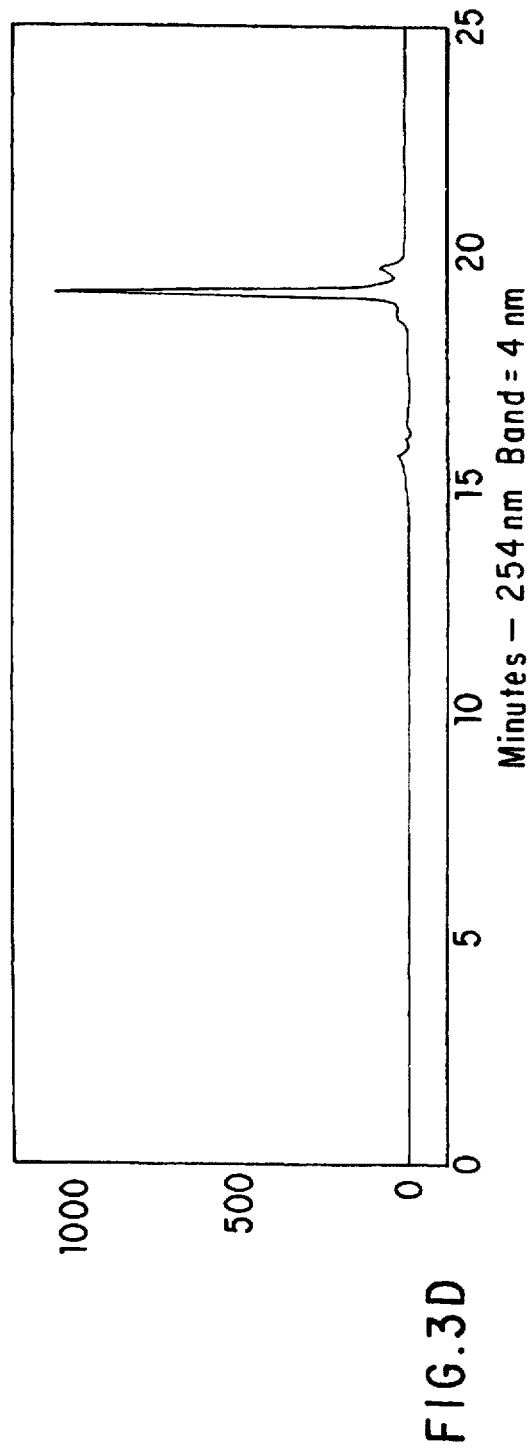
Figure 3E:
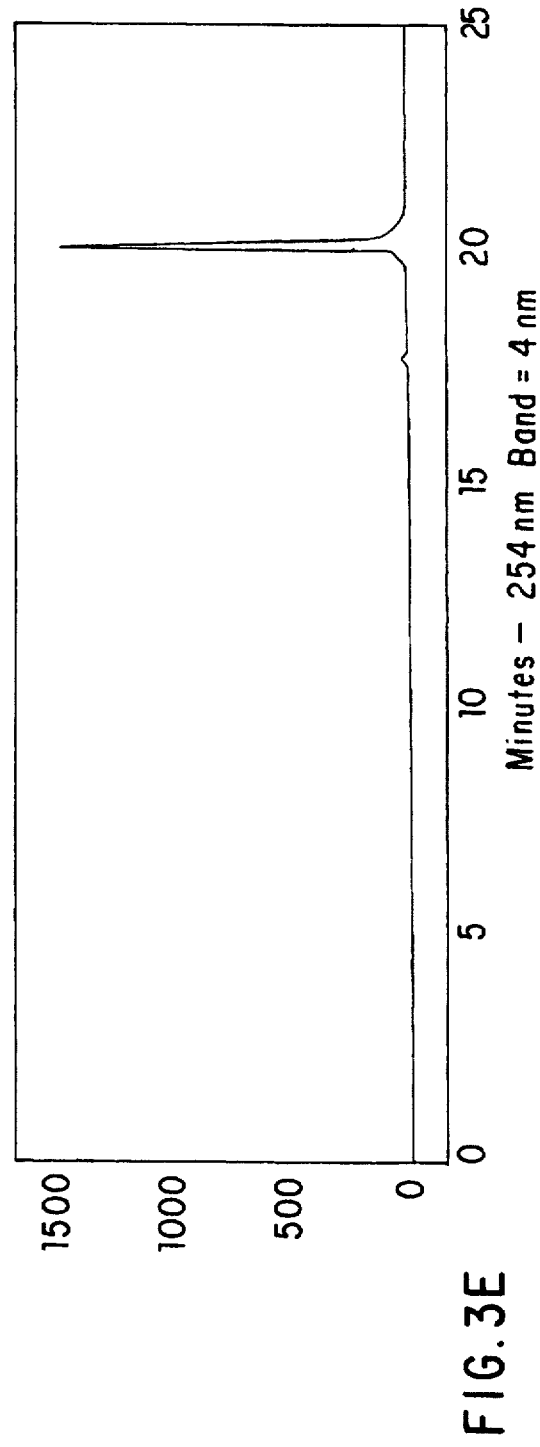

Graphic representations of the data are given in FIGS. 1–3. These figures represent the chromatograms and visually demonstrate the effectiveness of the present method.

These results demonstrate that the method by which molecules of interest are first combined and then purified is an effective method of separation.

The preceding example was repeated using another set of imidazolones consisting of 4-(4-ethylbenzylidene)-1-(2-hydroxyethyl)-2-phenyl-5(4H)-imidazolone (denoted F), 4-(3-methylbenzylidene)-1-(methyl-(2-tetrahydrofuryl))-2-phenyl-5(4H)-imidazolone (denoted G), 4-(3-methylbenzylidene)-1-phenylmethyl-2-phenyl-5(4H)-imidazolone (denoted H), and 4-(4-ethylbenzylidene)-1-(1-naphthyl)-2-phenyl-5(4H)-imidazolone (denoted I) which varied in purity as synthesized from 47–76% by HPLC analysis. This data is shown in Tables 12–15.

TABLE 12

| Peak Number | Retention Time | Area Percent |
| --- | --- | --- |
| 1 | 3.08 | 0.56 |
| 2 | 3.15 | 0.92 |
| 3 | 10.91 | 24.23 |
| 4 | 12.30 | 3.89 |
| 5 | 13.01 | 1.21 |
| 6 | 13.46 | 1.52 |
| 7 | 14.22 | 64.84 |
| 8 | 15.94 | 2.84 |

TABLE 13

| Peak Number | Retention Time | Area Percent |
| --- | --- | --- |
| 1 | 3.08 | 0.44 |
| 2 | 3.15 | 1.26 |
| 3 | 4.16 | 3.36 |
| 4 | 6.23 | 1.25 |
| 5 | 8.61 | 1.64 |
| 6 | 10.50 | 1.19 |
| 7 | 13.48 | 25.49 |
| 8 | 16.58 | 63.33 |
| 9 | 16.99 | 2.04 |

TABLE 14

| Peak Number | Retention Time | Area Percent |
| --- | --- | --- |
| 1 | 3.08 | 0.31 |
| 2 | 3.15 | 0.93 |
| 3 | 8.29 | 4.15 |
| 4 | 8.62 | 1.01 |
| 5 | 10.29 | 1.03 |
| 6 | 10.56 | 3.03 |
| 7 | 15.38 | 1.16 |
| 8 | 16.29 | 27.71 |
| 9 | 17.59 | 1.31 |
| 10 | 18.38 | 10.41 |
| 11 | 18.44 | 47.44 |
| 12 | 19.70 | 1.53 |

TABLE 15

| Peak Number | Retention Time | Area Percent |
| --- | --- | --- |
| 1 | 2.70 | 0.02 |
| 2 | 10.35 | 9.80 |
| 3 | 12.69 | 2.67 |
| 4 | 17.93 | 1.58 |
| 5 | 18.15 | 1.43 |
| 6 | 18.49 | 3.65 |
| 7 | 19.25 | 1.32 |
| 8 | 19.71 | 1.25 |
| 9 | 19.96 | 0.98 |
| 10 | 20.36 | 76.32 |
| 11 | 21.40 | 0.98 |

Combination of a 20 mg sample of each and application to a Zorbax ODS-SB RPC-18 column (25×250 mm), followed by elution with a 25–100% acetonitrile-1% TFA:water gradient afforded samples F–I in a purified form range from 95–99% in purity and eluting at 31.2, 37.6, 42.1 and 47.0 minutes. This data is shown in Tables 16–20.

TABLE 16

| Peak No. | Time | Type | Height (μV) | Area (μV-sec) | Area |
|---|---|---|---|---|---|
| 1 | 21.690 | N | 5628 | 100973 | 0.093 |
|   | 23.423 | N | 646 | 8932 | 0.008 |
| 2 | 24.013 | N | 3715 | 73470 | 0.068 |
| 3 | 26.165 | N | 28671 | 1316715 | 1.224 |
| 4 | 28.116 | N1 | 12906 | 457401 | 0.425 |
| 5 | 28.751 | N2 | 14267 | 36850 | 0.338 |
| 6 | 30.181 | N3 | 16316 | 722004 | 0.671 |
| 7 | 31.238 | N4 | 395451 | 28155410 | 26.179 |
| 8 | 33.510 | N5 | 7827 | 176187 | 0.163 |
|   | 24.021 | N6 | 909 | 2168 | 0.002 |
| 9 | 35.638 | N1 | 37569 | 1652023 | 1.536 |
| 10 | 37.556 | N2 | 395539 | 30071292 | 27.960 |
| 11 | 40.036 | N3 | 62577 | 3573319 | 3.322 |
| 12 | 41.118 | N4 | 20645 | 215890 | 0.200 |
| 13 | 41.345 | N5 | 21146 | 559845 | 0.520 |
| 14 | 42.126 | N6 | 400632 | 22544290 | 20.92 |
| 15 | 44.320 | N7 | 21642 | 572148 | 0.531 |
| 16 | 44.475 | N8 | 22374 | 221193 | 0.205 |
| 17 | 45.068 | N9 | 75664 | 2466974 | 2.293 |
| 18 | 45.976 | N10 | 26719 | 1049299 | 0.975 |
| 19 | 47.033 | N11 | 406058 | 13051508 | 12.135 |
| 20 | 49.288 | N12 | 5770 | 138795 | 0.129 |
| 21 | 49.885 | N13 | 2640 | 54304 | 0.050 |
| TotalArea |   |   |   | 107547990 | 99.989 |

TABLE 17

| Peak Number | Retention Time | Area Percent |
|---|---|---|
| 1 | 2.70 | 0.01 |
| 2 | 11.08 | 3.48 |
| 3 | 14.21 | 96.51 |

TABLE 18

| Peak Number | Retention Time | Area Percent |
|---|---|---|
| 1 | 3.01 | 0.01 |
| 2 | 12.78 | 0.91 |
| 3 | 13.63 | 2.11 |
| 4 | 14.25 | 1.99 |
| 5 | 16.53 | 94.99 |

TABLE 19

| Peak Number | Retention Time | Area Percent |
|---|---|---|
| 1 | 2.92 | 0.00 |
| 2 | 16.33 | 2.64 |
| 3 | 17.78 | 0.36 |
| 4 | 18.42 | 96.00 |

TABLE 20

| Peak Number | Retention Time | Area Percent |
|---|---|---|
| 1 | 2.90 | 0.00 |
| 2 | 18.47 | 1.26 |
| 3 | 20.38 | 98.73 |

What is claimed is:

1. A method for purifying molecules which comprises:

determining one or more selection parameters for a plurality of molecules;

selecting a compatible grouping of molecules based on said selection parameters to form a set;

combining a mixture of compatible crude molecules of interest from the set, wherein the molecules are derived from parallel syntheses; and resolving the mixture based on at least one of the selection parameters to fractionate the mixture by simultaneous preparative chromatography processing, separating each molecule of interest from the other molecules of interest in the mixture, increasing the purity of each molecule of interest.

2. The method according to claim 1 which further comprises determining at least one selection parameter for a molecule experimentally.

3. The method according to claim 2 which further comprises determining all selection parameters experimentally.

4. The method according to claim 1 wherein the selection step comprises selecting a group of molecules that have differing binding capabilities to form the set.

5. The method according to claim 4 which further comprises screening the mixture after the resolving step for a desired interaction that depletes one or more of the molecules of interest from the mixture, and re-analyzing the resultant mixture of molecules which did not bind to determine the molecule of interest participating in the desired reaction.

6. The method according to claim 5, wherein the selection parameters for the molecules of interest are sufficiently distinct to enable the amounts of such molecules to be experimentally determined from the mixture.

7. The method according to claim 6 wherein the molecules of interest have different retention times and the analyzing and re-analyzing steps are conducted on a HPLC column.

8. The method according to claim 1, further comprising determining a chromatographic retention time for each molecule in the mixture as the selection parameter, and fractionating the mixture chromatographically, based on the retention time of each molecule in the mixture, to increase the purity of all of the molecules of interest.

9. The method according to claim 8, wherein the purity of the crude molecules is increased by chromatographically separating the mixture on an HPLC column.

10. A method for the time resolution of molecules which comprises:

determining the retention time on a chromatography system for each molecule of interest in a plurality of molecules;

selecting a compatible grouping of crude molecules to form a set on the basis of retention time, resolvability, and system parameters;

combining a mixture of the compatible crude molecules of interest from the set, wherein the molecules are derived from parallel syntheses;

simultaneously preparative chromatographing the mixture to provide separation and purification of the molecules of interest based on their retention times;

collecting the fractions which contain the molecules of interest; and verifying analytically the identity of the molecule of interest in each fraction.

11. The method according to claim 10 which further comprises forming a compatible grouping of between 4 and 12 molecules of interest based on distinct retention times of each target molecule of the grouping; mixing the grouping of molecules; and chromatographically separating the mixture to increase the purity of at least some of the target molecules therein.

12. The method according to claim 11 wherein the mixture is chromatographically separated to increase the purity of all of the target molecules therein.

13. The method according to claim 10 wherein the chromatography system is a HPLC system and which further comprises forming a compatible grouping of between 4 and 12 crude molecules of interest based on distinct retention times of each target molecule of the grouping; mixing the grouping of molecules; and chromatographically separating the mixture on a HPLC column to increase the purity of at least some of the target molecules therein.

14. The method according to claim 13 wherein the mixture is chromatographically separated on the HPLC column to increase the purity of all of the target molecules therein.

15. The method according to claim 13 wherein the compatible grouping includes between 4 to 6 crude molecules of interest, at least one of which is chromatographically separated to increase the purity of that molecule to at least 65%.

16. The method according to claim 15 wherein the purity of at least some of the crude molecules of interest is increased to about 80%.

17. The method according to claim 15 wherein the purity of all of the crude molecules of interest is increased to at least about 80%.

18. The method according to claim 13 wherein the retention time of each target molecule is between 15 and 90 seconds different from the retention time of any other target molecule.

19. The method according to claim 13 wherein the retention time of each target molecule is between 15 and 90 seconds different from the retention time of any other molecule.

* * * * *